US011883630B2

(12) United States Patent
Dassau et al.

(10) Patent No.: US 11,883,630 B2
(45) Date of Patent: Jan. 30, 2024

(54) EVENT-TRIGGERED MODEL PREDICTIVE CONTROL FOR EMBEDDED ARTIFICIAL PANCREAS SYSTEMS

(71) Applicant: PRESIDENT AND FELLOWS OF HARVARD COLLEGE, Cambridge, MA (US)

(72) Inventors: Eyal Dassau, Acton, MA (US); Francis J. Doyle, III, Chestnut Hill, MA (US); Stamatina Zavitsanou, Cambridge, MA (US); Ankush Chakrabarty, Boston, MA (US)

(73) Assignee: PRESIDENT AND FELLOWS OF HARVARD COLLEGE

( * ) Notice: Subject to any disclaimer, the term of this patent is extended or adjusted under 35 U.S.C. 154(b) by 760 days.

(21) Appl. No.: 16/314,737

(22) PCT Filed: Jul. 6, 2017

(86) PCT No.: PCT/US2017/040835
§ 371 (c)(1),
(2) Date: Jan. 2, 2019

(87) PCT Pub. No.: WO2018/009614
PCT Pub. Date: Jan. 11, 2018

(65) Prior Publication Data
US 2022/0257857 A1    Aug. 18, 2022

Related U.S. Application Data

(60) Provisional application No. 62/508,526, filed on May 19, 2017, provisional application No. 62/359,098, filed on Jul. 6, 2016.

(51) Int. Cl.
*A61M 5/172*    (2006.01)
*G16H 20/17*    (2018.01)

(52) U.S. Cl.
CPC .......... *A61M 5/1723* (2013.01); *G16H 20/17* (2018.01); *A61M 2205/52* (2013.01); *A61M 2230/201* (2013.01)

(58) Field of Classification Search
CPC ............ G16H 20/17; A61M 2230/201; A61M 2205/52; A61M 5/1723
See application file for complete search history.

(56) References Cited

U.S. PATENT DOCUMENTS 5,746,697 A * 5/1998 Swedlow ........... A61B 5/14551
                                              600/323
10,117,992 B2  11/2018 Parikh et al.
(Continued)

OTHER PUBLICATIONS

Beck et al., Frequency of Morning Ketosis After Overnight Insulin Suspension Using an Automated Nocturnal Predictive Low Glucose Suspend System, 37(5) DIABETES CARE 1124-1229 (Year: 2014).*
(Continued)

*Primary Examiner* — Evangeline Barr
*Assistant Examiner* — Jordan L Jackson
(74) *Attorney, Agent, or Firm* — NIXON PEABODY LLP; David S. Resnick; Wayne L. Tang

(57) ABSTRACT

The development of artificial pancreas (AP) technology for deployment in low-energy, embedded devices is contingent upon selecting an efficient control algorithm for regulating glucose in people with type 1 diabetes mellitus (T1DM). The energy consumption of the AP can be lowered by reducing updates of the control model: the number of times the decisionmaking algorithm is invoked to compute an appropriate insulin dose.

19 Claims, 23 Drawing Sheets

(56) References Cited

U.S. PATENT DOCUMENTS

| | | |
|---|---|---|
| 10,546,659 B2 | 1/2020 | Kovatchev et al. |
| 2004/0158232 A1 | 8/2004 | Schetky et al. |
| 2005/0044436 A1* | 2/2005 | Holle ............... G06F 1/3228 713/320 |
| 2005/0272640 A1 | 12/2005 | Doyle et al. |
| 2007/0016127 A1 | 1/2007 | Staib et al. |
| 2007/0244575 A1 | 10/2007 | Wojsznis et al. |
| 2007/0276512 A1 | 11/2007 | Fan et al. |
| 2008/0033271 A1 | 2/2008 | Say et al. |
| 2008/0208113 A1 | 8/2008 | Damiano et al. |
| 2008/0235053 A1 | 9/2008 | Ray et al. |
| 2009/0143725 A1 | 6/2009 | Peyser et al. |
| 2009/0315772 A1 | 12/2009 | Wengler et al. |
| 2010/0198142 A1 | 8/2010 | Sloan et al. |
| 2010/0262117 A1* | 10/2010 | Magni ............... G16H 20/17 604/504 |
| 2010/0280441 A1 | 11/2010 | Wilinska et al. |
| 2010/0298685 A1 | 11/2010 | Hayter et al. |
| 2011/0098548 A1 | 4/2011 | Budiman et al. |
| 2011/0106011 A1 | 5/2011 | Cinar et al. |
| 2011/0208156 A1 | 8/2011 | Doyle et al. |
| 2013/0018232 A1 | 1/2013 | D'Souza et al. |
| 2014/0005633 A1 | 1/2014 | Finan |
| 2014/0081236 A1 | 3/2014 | Wilinska et al. |
| 2014/0121488 A1 | 5/2014 | Budiman |
| 2014/0180240 A1 | 6/2014 | Finan et al. |
| 2014/0200559 A1 | 7/2014 | Doyle et al. |
| 2014/0276554 A1* | 9/2014 | Finan ............... A61M 5/14244 604/504 |
| 2014/0276555 A1 | 9/2014 | Morales |
| 2014/0379273 A1 | 12/2014 | Petisce et al. |
| 2015/0100038 A1 | 4/2015 | McCann et al. |
| 2015/0134356 A1 | 5/2015 | Atlas et al. |
| 2015/0309486 A1 | 10/2015 | Webersinke et al. |
| 2016/0030670 A1 | 2/2016 | Fischl |
| 2016/0038673 A1 | 2/2016 | Morales |
| 2016/0048119 A1 | 2/2016 | Wojsznis et al. |
| 2016/0163037 A1 | 6/2016 | Dehais et al. |
| 2016/0170384 A1 | 6/2016 | Charest-Finn et al. |
| 2016/0281489 A1 | 9/2016 | Dykstra et al. |
| 2017/0000943 A1 | 1/2017 | Blomquist et al. |
| 2017/0017212 A1 | 1/2017 | Collins et al. |
| 2017/0099011 A1* | 4/2017 | Freeman ............... H02M 7/06 |
| 2017/0136160 A1 | 5/2017 | Barral et al. |
| 2017/0143899 A1 | 5/2017 | Gondhalekar et al. |
| 2017/0173262 A1 | 6/2017 | Veltz |
| 2017/0192400 A1 | 7/2017 | Hofschulz et al. |
| 2017/0216518 A1 | 8/2017 | Davis et al. |
| 2017/0249445 A1 | 8/2017 | Devries et al. |
| 2018/0147349 A1 | 5/2018 | Finan et al. |
| 2018/0369479 A1 | 12/2018 | Hayter et al. |
| 2020/0268968 A1 | 8/2020 | Steil et al. |

OTHER PUBLICATIONS

Turksoy et al, An Integrated Multivariable Artificial Pancreas Control System, 8(3) J of Diabetes Science and Tech 498-507 (Year: 2014).*

McGraw-Hill Dictionary of Scientific & Technical Terms, 6E (Sep. 26, 2002) (Year: 2002).*

Li and Tan, An Ultra-low-power Medium Access Control Protocol for Body Sensor Network, Engineering in Medicine and Biology 27th Annual Conference 2451-2454 (Year: 2005).*

Grosman et al., Zone Model Predictive Control: A Strategy to Minimize Hyper- and Hypoglycemic Events, 4(4) J of Diabetes Science and Technology 961-975 (Jul. 2010) (Year: 2010).*

Banerjee et al. "Model based safety analysis and verification of cyber-physical systems" Dissertation, Arizona State University (2012).

Grosman et al., "Zone model predictive control: a strategy to minimize hyper- and hypoglycemic events" Journal of diabetes science and technology 4(4): 961-975 (2010).

Gonzalez et al., "A stable MPC with zone control", Journal of Process Control 19(1):110-122 (2009).

Lee et al., "A Closed-loop Artificial Pancreas based on the MPC: human friendly identification and automatic meal disturbance rejection." IFAC Proceedings vols. 41(2): 4252-4257 (2008).

Charest et al., "MPC enhancement for tracking of complex profiles—The basic technique." Control Engineering Practice 33: 136-147 (2014).

Van Heusden et al., "Control-Relevant Models for Glucose Control Using a priori patient characteristics." IEEE transactions on biomedical engineering 59(7): 1839-1849 (2011).

Wang et al., "Automatic Bolus and Adaptive basal algorithm for the artificial pancreatic β-cell." Diabetes technology & therapeutics 12(11): 879-887 (2010).

Seborg et al., "Chapter 20, Model Predictive Control", 2011 pp. 414-438.

Enso "Model Predictive Control and State Estimation", 2013, pp. 112.

Domanski et al., "Assessment of predictive control performance using fractal measures." Nonlinear Dynamics 89(2): 773-790 (2017).

Lee et al., "Enhanced model predictive control (eMPC) strategy for automated glucose control." Industrial & engineering chemistry research 55(46): 11857-11868 (2016).

Cameron et al., "A closed-loop artificial pancreas based on risk management." Journal of diabetes science and technology 5(2): 368-379 (2011).

Messori et al., "A constrained model predictive controller for an artificial pancreas." IFAC Proceedings vols. 47(3):10144-10149 (2014).

Hu et al., "An improved PID algorithm based on insulin-on-board estimate for blood glucose control with Type 1 diabetes." Computational and Mathematical Methods in Medicine 2015(281589):1-9 (2015).

Tiagounov "High-performance model predictive control for process industry." Technische Universiteit Eindhoven, Eindhoven, Netherlands (2004).

Gonzalez et al., "Model predictive control tuning based on Extended Kalman Filter." 2017 IEEE Second Ecuador Technical Chapters Meeting (ETCM). IEEE, 2017.

Soru et al., "MPC based artificial pancreas: strategies for individualization and meal compensation." Annual Reviews in Control 36.1 (2012): 118-128.

Thabit et al. "Coming of age: the artificial pancreas for type 1 diabetes." Diabetologia 59(9): 1795-1805 (2016).

Toffanin et al. "Dynamic insulin on board: incorporation of circadian insulin sensitivity variation." Journal of diabetes science and technology 7(4): 928-940 (2013).

Toffanin et al. "Artificial pancreas: model predictive control design from clinical experience." Journal of Diabetes Science and Technology 7(6):1470-1483 (2013).

Trimpe et al. "A self-tuning Lqr approach demonstrated on an inverted pendulum." IFAC Proceedings vols. 47(3): 11281-11287 (2014).

Trogmann et al. "Hybrid control of type 1 diabetes bolus therapy." 49th IEEE Conference on Decision and Control (CDC). IEEE. 4721-4726 (2010).

Turksoy et al. "Multivariable adaptive identification and control for artificial pancreas systems." IEEE Transactions on Biomedical Engineering 61(3): 883-891 (2013).

Turksoy et al. "Adaptive control of artificial pancreas systems—a review." Journal of healthcare engineering 5(1): (2014) 1-22.

Tvarijonaviciute et al. "Obesity-related metabolic dysfunction in dogs: a comparison with human metabolic syndrome." BMC Veterinary Research 8(1): 1-8 (2012).

Valderas et al. "Acarbose improves hypoglycaemia following gastric bypass surgery without increasing glucagon-like peptide 1 levels." Obesity surgery 22(4): 582-586 (2012).

Van Bon et al. "Feasibility of a portable bihormonal closed-loop system to control glucose excursions at home under free-living conditions for 48 hours." Diabetes technology & therapeutics 16(3): 131-136 (2014).

Van Dijk et al. "Intraperitoneal insulin infusion: treatment option for type 1 diabetes resulting in beneficial endocrine effects beyond glycaemia." Clinical endocrinology 81(4): 488-497 (2014).

(56) References Cited

OTHER PUBLICATIONS

Van Dijk et al. "Continuous intraperitoneal insulin infusion versus subcutaneous insulin therapy in the treatment of type 1 diabetes: effects on glycemic variability." Diabetes technology & therapeutics 17(6): 379-384 (2015).
Van Dijk et al. "Different effects of intraperitoneal and subcutaneous insulin administration on the GH-IGF-1 axis in type 1 diabetes." The Journal of Clinical Endocrinology & Metabolism 101(6): 2493-2501 (2016).
Vukmir et al. "Glucagon: prehospital therapy for hypoglycemia." Annals of emergency medicine 20(4): 375-379 (1991).
Wang et al. "Closed-loop control of artificial pancreatic beta-cell in type 1 diabetes mellitus using model predictive iterative learning control." IEEE Transactions on Biomedical Engineering 57(2): 211-219 (2009).
Wang et al. "Survey on iterative learning control, repetitive control, and run-to-run control." Journal of Process Control 19(10): 1589-1600 (2009).
Yeh et al. "Comparative effectiveness and safety of methods of insulin delivery and glucose monitoring for diabetes mellitus: a systematic review and meta-analysis." Annals of internal medicine 157(5): 336-347 (2012).
Yen et al. "Effect of somatostatin in patients with acromegaly: suppression of growth hormone, prolactin, insulin and glucose levels." New England Journal of Medicine 290(17): 935-938 (1974).
Zisser et al. "Run-to-run control of meal-related insulin dosing." Diabetes technology & therapeutics 7(1): 48-57 (2005).
Zisser et al. "Clinical results of an automated artificial pancreas using technosphere inhaled insulin to mimic first-phase insulin secretion." Journal of diabetes science and technology 9(3): 564-572 (2015).
Myers et al. "Intraportal glucose delivery enhances the effects of hepatic glucose load on net hepatic glucose uptake in vivo." The Journal of clinical investigation 88(1): 158-167 (1991).
Myint et al. "Prolonged successful therapy for hyperinsulinaemic hypoglycaemia after gastric bypass: the pathophysiological role of GLP1 and its response to a somatostatin analogue." European Journal of Endocrinology 166(5): 951-955 (2012).
Newswanger et al. "Development of a highly stable, nonaqueous glucagon formulation for delivery via infusion pump systems." Journal of diabetes science and technology 9(1): 24-33 (2015).
Nimri et al. "MD-Logic overnight control for 6 weeks of home use in patients with type 1 diabetes: randomized crossover trial." Diabetes care 37(11): 3025-3032 (2014).
Norrlof. "Iterative Learning Control—Analysis, Design, and Experiments." Thesis No. 653, Linkoping Univ., Linkoping, Sweden (2000)
Owens et al. "Run-to-run control of blood glucose concentrations for people with type 1 diabetes mellitus." IEEE Transactions on Biomedical Engineering 53(6): 996-1005 (2006).
Palerm et al. "A run-to-run framework for prandial insulin dosing: handling real-life uncertainty." International Journal of Robust and Nonlinear Control: IFAC-Affiliated Journal 17(13): 1194-1213 (2007).
Palerm et al. "A run-to-run control strategy to adjust basal insulin infusion rates in type 1 diabetes." Journal of processcontrol 18(3-4): 258-265 (2008).
Palerm. "Physiologic insulin delivery with insulin feedback: a control systems perspective." Computer methods and programsin biomedicine102(2): 130-137 (2011).
Panteleon et al. "Quantification of delays associated with intraperitoneal insulin delivery and IV glucose sensing aiming at closed loop insulin delivery." Diabetes vol. 53(1701): Abstract 446-P (2004).
Panteleon et al. "Evaluation of the effect of gain on the meal response of an automated closed-loop insulin delivery system." Diabetes 55(7): 1995-2000 (2006).
Parker et al. "Advanced model predictive control (MPC) for type I diabetic patient blood glucose control." Proceedings of the 2000 American Control Conference. ACC. vol. 5. IEEE. 3483-3487(2000).

Patek et al., "Linear quadratic gaussian-based closed-loop control of type 1 diabetes", Journal of Diabetes Science and Technology 1(6): 834-841 (2007).
Patek et al. "Modular closed-loop control of diabetes." IEEE Transactions on Biomedical Engineering 59(11): 2986-2999 (2012).
Patti et al. "Hypoglycemia after gastric bypass: the dark side of GLP-1." Gastroenterology 146(3): 605-608 (2014).
Patti et al. "Insulin response to oral stimuli and glucose effectiveness increased in neuroglycopenia following gastric bypass." Obesity 23(4): 798-807 (2015).
Pernar et al. "Gastric bypass reversal: a 7-year experience." Surgery for Obesity and Related Diseases 12(8): 1492-1498 (2016).
Pickup. "Insulin pumps," Diabetes technology & therapeutics 18(S1): S22-S28 (2016).
Pinsker et al. "Randomized crossover comparison of personalized MPC and PID control algorithms for the artificial pancreas." Diabetes Care 39(7): 1135-1142 (2016).
Ranjan et al. "Effects of subcutaneous, low-dose glucagon on insulin-induced mild hypoglycaemia in patients with insulin pump treated type 1 diabetes." Diabetes, Obesity and Metabolism 18(4): 410-418 (2016).
Reddy et al. "Metabolic control with the bio-inspired artificial pancreas in adults with type 1 diabetes: a 24-hour randomized controlled crossover study." Journal of diabetes science and technology 10(2): 405-413 (2016).
Renard et al. "Complications of the pump pocket may represent a significant cause of incidents with implanted systems for intraperitoneal insulin delivery." Diabetes Care 17(9): 1064-1066 (1994).
Renard et al. "Insulin underdelivery from implanted pumps using peritoneal route: determinant role of insulin pump compatibility." Diabetes Care 19(8): 812-817 (1996).
Renard et al. "Artificial β-cell: clinical experience toward an implantable closed-loop insulin delivery system." Diabetes & metabolism 32(5): 497-502 (2006).
Renard et al. "Closed-loop insulin delivery using a subcutaneous glucose sensor and intraperitoneal insulin delivery: feasibility study testing a new model for the artificial pancreas." Diabetes care 33(1): 121-127 (2010).
Renard et al. "Lower rate of initial failures and reduced occurrence of adverse events with a new catheter model for continuous subcutaneous insulin infusion: prospective, two-period, observational, multicenter study." Diabetes technology & therapeutics 12(10): 769-773 (2010).
Reubi et al. "Distribution of somatostatin receptors in normal and tumor tissue." Metabolism 39(9): 78-81 (1990).
Richter et al. "Computational complexity certification for real-time MPC with input constraints based on the fast gradient method." IEEE Transactions on Automatic Control 57(6): 1391-1403 (2012).
Rivera et al., "Internal model control: PID controller design." Ind. Eng. Chem. Process Des. Dev. 25: 252-265 (1986).
Rohlfing et al. "Defining the relationship between plasma glucose and HbA1c: analysis of glucose profiles and HbA1c in the Diabetes Control and Complications Trial." Diabetes care 25(2): 275-278 (2002).
Ruiz et al. "Effect of insulin feedback on closed-loop glucose control: a crossover study." Journal of diabetes science and technology 6(5): (2012): 1123-1130.
Russell et al. "Day and night glycaemic control with a bionic pancreas versus conventional insulin pump therapy in preadolescent children with type 1 diabetes: a randomised crossover trial." The lancet Diabetes & endocrinology 4(3): 233-243 (2016).
Salehi et al. "Blockade of glucagon-like peptide 1 receptor corrects postprandial hypoglycemia after gastric bypass." Gastroenterology 146(3): 669-680 (2014).
Salehi et al. "Altered islet function and insulin clearance cause hyperinsulinemia in gastric bypass patients with symptoms of postprandial hypoglycemia." The Journal of Clinical Endocrinology & Metabolism 99(6): 2008-2017 (2014).
Sarwar et al. "Hypoglycemia after Roux-en-Y gastric bypass: the BOLD experience." Obesity surgery 24(7): 1120-1124 (2014).
Scavini et al. "Intraperitoneal Insulin Absorption After Lona-Term Intraperitoneal Insulin Therapy." Diabetes care 18(1): 56-59 (1995).

(56) References Cited

OTHER PUBLICATIONS

Schaepelynck et al. "A recent survey confirms the efficacy and the safety of implanted insulin pumps during long-term use in poorly controlled type 1 diabetes patients." Diabetes technology & therapeutics 13(6): 657-660 (2011).

Schauer et al. "Bariatric surgery versus intensive medical therapy for diabetes—3-year outcomes." New England Journal of Medicine 370(21): 2002-2013 (2014).

Schmelzeisen-Redeker et al. "Time delay of CGM sensors: relevance, causes, and countermeasures." Journal of diabetes science and technology 9(5): 1006-1015 (2015).

Seita et al. "Development of canine models of type 1 diabetes with partial pancreatectomy and the administration of streptozotocin." Cell Medicine 6.(1-2): 25-31 (2013).

Shahriari et al. "Taking the human out of the loop: A review of Bayesian optimization." Proceedings of the IEEE 104(1): 148-175 (2015).

Shapiro et al. "An analysis of variance test for normality (complete samples)." Biometrika 52(3/4): 591-611 (1965).

Soon-Shiong et al. "Successful reversal of spontaneous diabetes in dogs by intraperitoneal microencapsulated islets." Transplantation 54(5): 769-774 (1992).

Spaan et al. "Implantable insulin pumps: an effective option with restricted dissemination." The Lancet Diabetes & Endocrinology 2(5): 358-360 (2014).

Steil et al. "Automated insulin delivery for type 1 diabetes." Current Opinion in Endocrinology, Diabetes and Obesity 13(2): 205-211 (2006).

Steil et al. "Feasibility of automating insulin delivery for the treatment of type 1 diabetes." Diabetes 55(12): 3344-3350 (2006).

Szücs et al. "A memory-efficient representation of explicit MPC solutions." 2011 50th IEEE Conference on Decision and Control and European Control Conference. IEEE. 1916-1921 (2011).

Tarin et al. "Comprehensive pharmacokinetic model of insulin glargine and other insulin formulations." IEEE Transactions on Biomedical Engineering 52(12): 1994-2005 (2005).

Tauschmann et al. "Day- and-night hybrid closed-loop insulin delivery in adolescents with type 1 diabetes: a free-living, randomized clinical trial." Diabetes Care 39(7): 1168-1174 (2016).

Thabit et al. "Home use of an artificial beta cell in type 1 diabetes." New England Journal of Medicine 373(22): 2129-2140 (2015).

Gondhalekar et al. "Tackling problem nonlinearities & delays via asymmetric, state-dependent objective costs in MPC of an artificial pancreas." IFAC-PapersOnLine 48(23): 154-159 (2015).

Gondhalekar et al. "Velocity-weighting to prevent controller-induced hypoglycemia in MPC of an artificial pancreas to treat T1DM." 2015 American Control Conference (ACC). IEEE. 1635-1640 (2015).

Gondhalekar et al. "Periodic zone-MPC with asymmetric costs for outpatient-ready safety of an artificial pancreas to treat type 1 diabetes." Automatica 71: 237-246 (2016).

Gonzalez-Gonzalez et al. "Use of diazoxide in management of severe postprandial hypoglycemia in patient after Roux-en-Y gastric bypass." Surgery for Obesity and Related Diseases 9(1): e18-e19 (2013).

Goodyear et al. "Exercise, glucose transport, and insulin sensitivity." Annual review of medicine 49(1): 235-261 (1998).

Gregory et al. "Insulin delivery into the peripheral circulation: a key contributor to hypoglycemia in type 1 diabetes." Diabetes 64(10): 3439-3451 (2015).

Grosman et al. "Multi-zone-MPC: Clinical inspired control algorithm for the artificial pancreas." IFAC Proceedings vols. 44(A1161): 7120-7125 (2011).

Grosman et al. "Hybrid closed-loop insulin delivery in type 1 diabetes during supervised outpatient conditions." Journal of diabetes science and technology 10(3): 708-713 (2016).

Halperin et al. "Glucagon treatment for post-gastric bypass hypoglycemia." Obesity 18(9): 1858-1860 (2010).

Halperin et al. "Continuous glucose monitoring for evaluation of glycemic excursions after gastric bypass." Journal of obesity (2011): Article 869536, 1-7 (2011).

Halperin et al. "Roux-en-Y gastric bypass surgery or lifestyle with intensive medical management in patients with type 2 diabetes: feasibility and 1-year results of a randomized clinical trial." JAMA surgery 149(7): 716-726 (2014).

Harvey et al. "Design of the health monitoring system for the artificial pancreas: low glucose prediction module." Journal of diabetes science and technology 6(6): 1345-1354 (2012).

Harvey et al. "Clinical evaluation of an automated artificial pancreas using zone-model predictive control and health monitoring system." Diabetes technology & therapeutics 16(6): 348-357 (2014).

Haymond et al. "Nonaqueous, mini-dose glucagon for treatment of mild hypoglycemia in adults with type 1 diabetes: a dose-seeking study." Diabetes Care 39(3): 465-468 (2016).

Heemels et al. "An introduction to event-triggered and self-triggered control." 2012 IEEE 51st IEEE conference on decision and control (CDC). IEEE:1-16 (2012).

Heise et al. "Insulin stacking versus therapeutic accumulation: understanding the differences." Endocrine Practice 20(1): 75-83 (2014).

Hepburn et al. "Symptoms of acute insulin-induced hypoglycemia in humans with and without IDDM: factor-analysis approach." Diabetes Care 14(11): 949-957 (1991).

Horton. "Exercise and physical training: effects on insulin sensitivity and glucose metabolism." Diabetes/metabolism reviews 2(1-2): 1-17 (1986).

Horwitz et al. "Proinsulin, insulin, and C-peptide concentrations in human portal and peripheral blood." The Journal of clinical investigation 55(6): 1278-1283 (1975).

Hovorka et al. "Nonlinear model predictive control of glucose concentration in subjects with type 1 diabetes." Physiological measurement 25(4): 905-920 (2004).

Hovorka. "Continuous glucose monitoring and closed-loop systems." Diabetic medicine 23(1): 1-12 (2006).

Huyett et al. "Design and evaluation of a robust PID controller for a fully implantable artificial pancreas." Industrial & engineering chemistry research 54(42): 10311-10321 (2015).

Jost et al. "Optimal and suboptimal event-triggering in linear model predictive control." 2015 European Control Conference (ECC). IEEE 14: 1147-1152 (2015).

Kellogg et al. "Postgastric bypass hyperinsulinemic hypoglycemia syndrome: characterization and response to a modified diet." Surgery for Obesity and Related Diseases 4(4): 492-499 (2008).

Kerfurt et al. "Hypoglycemia after Roux-En-Y gastric bypass: detection rates of continuous glucose monitoring (CGM) versus mixed meal test." Surgery for Obesity and Related Diseases 11(3): 564-569 (2015).

Kirchsteiger et al. "Robustness properties of optimal insulin bolus administrations for type 1 diabetes." American Control Conference. IEEE: 2284-2289 (2009).

Knab et al. "Zone model predictive control and moving horizon estimation for the regulation of blood glucose in critical care patients." IFAC-PapersOnLine 48(8): 1002-1007 (2015).

Koerker et al. "Somatostatin: hypothalamic inhibitor of the endocrine pancreas." Science 184(4135): 482-484 (1974).

Kovatchev et al. "In silico preclinical trials: a proof of concept in closed-loop control of type 1 diabetes." Journal of Diabetes Science and Technology3(1): 44-55 (2009).

Kovatchev et al. "Safety of outpatient closed-loop control: first randomized crossover trials of a wearable artificial pancreas." Diabetes care 37(7): 1789-1796 (2014).

Lee et al. "Design and in silico evaluation of an intraperitoneal-subcutaneous (IP-SC) artificial pancreas." Computers & chemical engineering 70: 180-188 (2014).

Lehmann et al. "Event-triggered model predictive control of discrete-time linear systems subject to disturbances." 2013 European Control Conference (ECC). IEEE:1-6 (2013).

Liebl et al. "A reduction in severe hypoglycaemia in type 1 diabetes in a randomized crossover study of continuous intraperitoneal compared with subcutaneous insulin infusion." Diabetes, obesity and metabolism 11(11): 1001-1008 (2009).

(56) References Cited

OTHER PUBLICATIONS

Liu et al. "Insulin is a stronger inducer of insulin resistance than hyperglycemia in mice with type 1 diabetes mellitus (T1DM)." Journal of Biological Chemistry 284(40): 27090-27100 (2009).
Ljung. "System identification." Signal analysis and prediction. Birkhäuser, Boston, MA, 163-173 (1998).
Longman. "Iterative learning control and repetitive control for engineering practice." International journal of control 73(10): 930-954 (2000).
Luo, "Machine learning of lifestyle data for diabetes." The University of Western Ontario. Electronic Thesis and Dissertation Repository, 3650 (2016).
Ly et al. "Day and night closed-loop control using the integrated Medtronic hybrid closed-loop system in type 1 diabetes at diabetes camp." Diabetes Care 38(7): 1205-1211 (2015).
Ly et al. "Automated overnight closed-loop control using a proportional-integral-derivative algorithm with insulin feedback in children and adolescents with type 1 diabetes at diabetes camp." Diabetes technology & therapeutics 18(6): 377-384 (2016).
Ly et al. "Automated hybrid closed-loop control with a proportional-integral-derivative based system in adolescents and adults with type 1 diabetes: individualizing settings for optimal performance." Pediatric diabetes 18(5): 348-355 (2017).
Maahs et al. "A randomized trial of a home system to reduce nocturnal hypoglycemia in type 1 diabetes." Diabetes care 37(7): 1885-1891 (2014).
Maahs et al. "Outcome measures for artificial pancreas clinical trials: a consensus report." Diabetes care 39(7): 1175-1179 (2016).
Magni et al. "Model predictive control of type 1 diabetes: an in silico trial." Journal of Diabetes Science and Technology1:(6) 804-812 (2007).
Magni et al. "Evaluating the efficacy of closed-loop glucose regulation via control-variability grid analysis." Journal of diabetes science and technology 2(4): 630-635 (2008).
Matsuo et al. "Strict glycemic control in diabetic dogs with closed-loop intraperitoneal insulin infusion algorithm designed for an artificial endocrine pancreas." Journal of Artificial Organs 6(1): 55-63 (2003).
McLaughlin et al. "Reversible hyperinsulinemic hypoglycemia after gastric bypass: a consequence of altered nutrient delivery." The Journal of Clinical Endocrinology & Metabolism 95(4): 1851-1855 (2010).
Mehta et al. "Impact of carbohydrate counting on glycemic control in children with type 1 diabetes." Diabetes Care 32(6): 1014-1016 (2009).
Mingrone et al. "Bariatric-metabolic surgery versus conventional medical treatment in obese patients with type 2 diabetes: 5 year follow-up of an open-label, single-centre, randomised controlled trial." The Lancet 386(9997): 964-973 (2015).
Moore. "Iterative learning control: An overview." Iterative Learning Control for Deterministic Systems (371): 9-22 (1993).
Moreira et al. "Post-prandial hypoglycemia after bariatric surgery: pharmacological treatment with verapamil and acarbose." Obesity surgery 18(12):1618-1621 (2008).
Abrahamsson et al. "Gastric bypass reduces symptoms and hormonal responses in hypoglycemia." Diabetes 65(9): 2667-2675 (2016).
Andersen et al. "Interior-point methods for large-scale cone programming." Optimization for machine learning 5583: 56-83 (2011).
Bell et al. "Impact of fat, protein, and glycemic index on postprandial glucose control in type 1 diabetes: implications for intensive diabetes management in the continuous glucose monitoring era." Diabetes care 38(6): 1008-1015 (2015).
Bemporad et al. "The explicit linear quadratic regulator for constrained systems." Automatica 38(1): 3-20 (2002).
Benosman et al. "Bayesian optimization-based modular indirect adaptive control for a class of nonlinear systems." IFAC-PapersOnLine 49(13): 253-258 (2016).
Bernardini et al. "Energy-aware robust model predictive control based on noisy wireless sensors." Automatica 48(1): 36-44 (2012).
Blauw et al. "Performance and safety of an integrated bihormonal artificial pancreas for fully automated glucose control at home." Diabetes, Obesity and Metabolism 18(7): 671-677 (2016).
Breton et al. "Fully integrated artificial pancreas in type 1 diabetes: modular closed-loop glucose control maintains near normoglycemia." Diabetes 61(9): 2230-2237 (2012).
Bristow et al. "A survey of iterative learning control." IEEE control systems magazine 26(3): 96-114 (2006).
Burnett et al. "Glucose sensing in the peritoneal space offers faster kinetics than sensing in the subcutaneous space." Diabetes 63(7): 2498-2505 (2014).
Cameron et al. "Extended multiple model prediction with application to blood glucose regulation," J. Process Control 22(8): 1422-1432 (2012).
Campos-Cornjeo et al. "An advisory protocol for rapid-and slow-acting insulin therapy based on a run-to-run methodology." Diabetes Technology & Therapeutics 12.7 (2010): 555-565.
Campos-Cornejo et al. "Adaptive control algorithm for a rapid and slow acting insulin therapy following run-to-run methodology." Proceedings of the 2010 American Control Conference. IEEE (2010).
Campos-Delgado et al. "Self-tuning insulin adjustment algorithm for type 1 diabetic patients based on multi-doses regime." Applied Bionics and Biomechanics 2(2): 61-71 (2005).
Campos-Delgado et al. "Fuzzy-based controller for glucose regulation in type-1 diabetic patients by subcutaneous route." IEEE Transactions on Biomedical Engineering 53(11): 2201-2210 (2006).
Ceriello et al. "Postprandial glucose regulation and diabetic complications." Archives of internal medicine 164(19): 2090-2095 (2004).
Cescon et al. "Impulsive predictive control of T1DM glycemia: an in-silico study." Dynamic Systems and Control Conference. American Society of Mechanical Engineers vol. (45295): 319-326 (2012).
Chakrabarty et al. "Support vector machine informed explicit nonlinear model predictive control using low-discrepancy sequences." IEEE Transactions on Automatic Control 62(1): 135-148 (2016).
Cherrington et al. "The role of insulin and glucagon in the regulation of basal glucose production in the postabsorptive dog." The Journal of clinical investigation 58(6): 1407-1418 (1976).
Cherrington. "Control of glucose uptake and release by the liver in vivo." Diabetes 48(5): 1198-1214 (1999).
Clark et al. "Even silent hypoglycemia induces cardiac arrhythmias." Diabetes 63(5): 1457-1459 (2014).
Colberg et al. "Pumping insulin during exercise: What healthcare providers and diabetic patients need to know." The physician and sportsmedicine 30(4): 33-38 (2002).
Colmegna et al. "Switched LPV glucose control in type 1 diabetes." IEEE Transactions on Biomedical Engineering 63(6): 1192-1200 (2016).
Dalla-Man et al. "GIM, simulation software of meal glucose-insulin model." Journal of Diabetes Science and Technology1(3): 323-330 (2007).
Dalla-Man et al. "Meal simulation model of the glucose-insulin system." IEEE Transactions on biomedical engineering 54(10): 1740-1749 (2007).
Dalla-Man et al. "The UVA/PADOVA type 1 diabetes simulator: new features." Journal of diabetes science and technology 8(1): 26-34 (2014).
Dassau et al. "Modular artificial β-cell system: a prototype for clinical research." Journal of Diabetes Science and Technology 2(5): 863-872 (2008).
Dassau et al. "In silico evaluation platform for artificial pancreatic β-cell development—a dynamic simulator for closed-loop control with hardware-in-the-loop." Diabetes technology & therapeutics 11(3): 187-194 (2009).
Dassau et al. "Real-time hypoglycemia prediction suite using continuous glucose monitoring: a safety net for the artificial pancreas." Diabetes care 33(6): 1249-1254 (2010).
Dassau et al. "Adjustment of open-loop settings to improve closed-loop results in type 1 diabetes: a multicenter randomized trial." The Journal of Clinical Endocrinology & Metabolism 100(10): 3878-3886 (2015).

(56) References Cited

OTHER PUBLICATIONS

Davidson et al. "Analysis of guidelines for basal-bolus insulin dosing: basal insulin, correction factor, and carbohydrate-to-insulin ratio." Endocrine Practice 14(9): 1095-1101 (2008).
Del Prato et al. "Effect of sustained physiologic hyperinsulinaemia and hyperglycemia on insulin secretion and insulin sensitivity in man." Diabetologia 37(10): 1025-1035 (1994).
Dobbins et al. "Compartmental modeling of glucagon kinetics in the conscious dog." Metabolism 44(4): 452-459 (1995).
Doyle III et al. "Closed-loop artificial pancreas systems: engineering the algorithms." Diabetes care 37(5): 1191-1197 (2014).
Eaton et al. "Hepatic removal of insulin in normal man: dose response to endogenous insulin secretion." The Journal of Clinical Endocrinology & Metabolism 56(6): 1294-1300 (1983).
Edgerton et al. "Small increases in insulin inhibit hepatic glucose production solely caused by an effect on glycogen metabolism." Diabetes 50(8): 1872-1882 (2001).
El-Khatib et al. "Adaptive closed-loop control provides blood-glucose regulation using dual subcutaneous insulin and glucagon infusion in diabetic swine." Journal of Diabetes Science and Technology 1(2): 181-192 (2007).
Ellingsen et al. "Safety constraints in an artificial pancreatic β cell: an implementation of model predictive control with insulin on board." Journal of diabetes science and technology 3(3): 536-544 (2009).
Eqtami et al. "Event-triggered control for discrete-time systems." Proceedings of the 2010 american control conference. IEEE. 4719-4724 (2010).
Eqtami et al. "Novel event-triggered strategies for model predictive controllers." 2011 50th IEEE Conference on Decision and Control and European Control Conference. IEEE. 1-7 (2011).
Eren-Oruklu et al. "Estimation of future glucose concentrations with subject-specific recursive linear models." Diabetes technology & therapeutics 11(4): 243-253 (2009).
Fernández-Esparrach et al. "Peroral endoscopic anastomotic reduction improves intractable dumping syndrome in Roux-en-Y gastric bypass patients." Surgery for Obesity and Related Diseases 6(1): 36-40 (2009).
Fritsch et al. "Monotone piecewise cubic interpolation: algorithms and software." Siam J. Numer. Anal. 17(2): 238-246 (1980).
Gillis et al. "Glucose estimation and prediction through meal responses using ambulatory subject data for advisory mode model predictive control." Journal of Diabetes Science and Technology 1(6): 825-833 (2007).
Gin et al. "Combined improvements in implantable pump technology and insulin stability allow safe and effective long term intraperitoneal insulin delivery in type 1 diabetic patients: the EVADIAC experience." Diabetes & metabolism 29(6): 602-607 (2003).
Goldfine et al. "Patients with neuroglycopenia after gastric bypass surgery have exaggerated incretin and insulin secretory responses to a mixed meal." The Journal of Clinical Endocrinology & Metabolism 92(12): 4678-4685 (2007).
Goldfine et al. "How common is hypoglycemia after gastric bypass?." Obesity (Silver Spring, Md.) 24(6): 1210-11 (2016).
Gondhalekar et al. "Periodic-zone model predictive control for diurnal closed-loop operation of an artificial pancreas." Journal of Diabetes Science and Technology 7(6): 1446-1460 (2013).
Gondhalekar et al. "Moving-horizon-like state estimation via continuous glucose monitor feedback in MPC of an artificial pancreas for type 1 diabetes." 53rd IEEE Conference on Decision and Control. IEEE. 310-315 (2014).
Gondhalekar et al. "MPC Design for Rapid Pump-Attenuation and Expedited Hyperglycemia Response to Treat T1DM with an Artificial Pancreas." Proc Am Control Conf 4224-4230 (2014).

\* cited by examiner

EVENT-TRIGGERED MODEL PREDICTIVE CONTROL FOR EMBEDDED ARTIFICIAL PANCREAS SYSTEMS

CROSS-REFERENCE TO RELATED APPLICATIONS

This application is a 35 U.S.C. § 371 National Phase Entry Application of International Application No. PCT/US2017/040835 filed Jul. 6, 2017, which designates the U.S. and claims benefit under 35 U.S.C. § 119(e) of U.S. Provisional Application Nos. 62/508,526 filed May 19, 2017 and 62/359,098 filed Jul. 6, 2016, the contents of which are incorporated herein by reference in their entirety.

STATEMENT REGARDING FEDERALLY SPONSORED RESEARCH OR DEVELOPMENT

This invention was made with government support under Grant Nos. DK104057 and DK101068 awarded by the National Institutes of Health. The government has certain rights in the invention.

FIELD

The present invention is directed to an artificial pancreas system and methods of control.

BACKGROUND

The following description includes information that may be useful in understanding the present invention. It is not an admission that any of the information provided herein is prior art or relevant to the presently claimed invention, or that any publication specifically or implicitly referenced is prior art.

An artificial pancreas helps people with diabetes automatically control their blood glucose level by providing the substitute endocrine functionality of a healthy pancreas. Specifically, it closely mimics the glucose regulating function of a healthy pancreas. System and methods are needed to make the artificial pancreas a longer lasting and more robust solution for glucose regulation.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
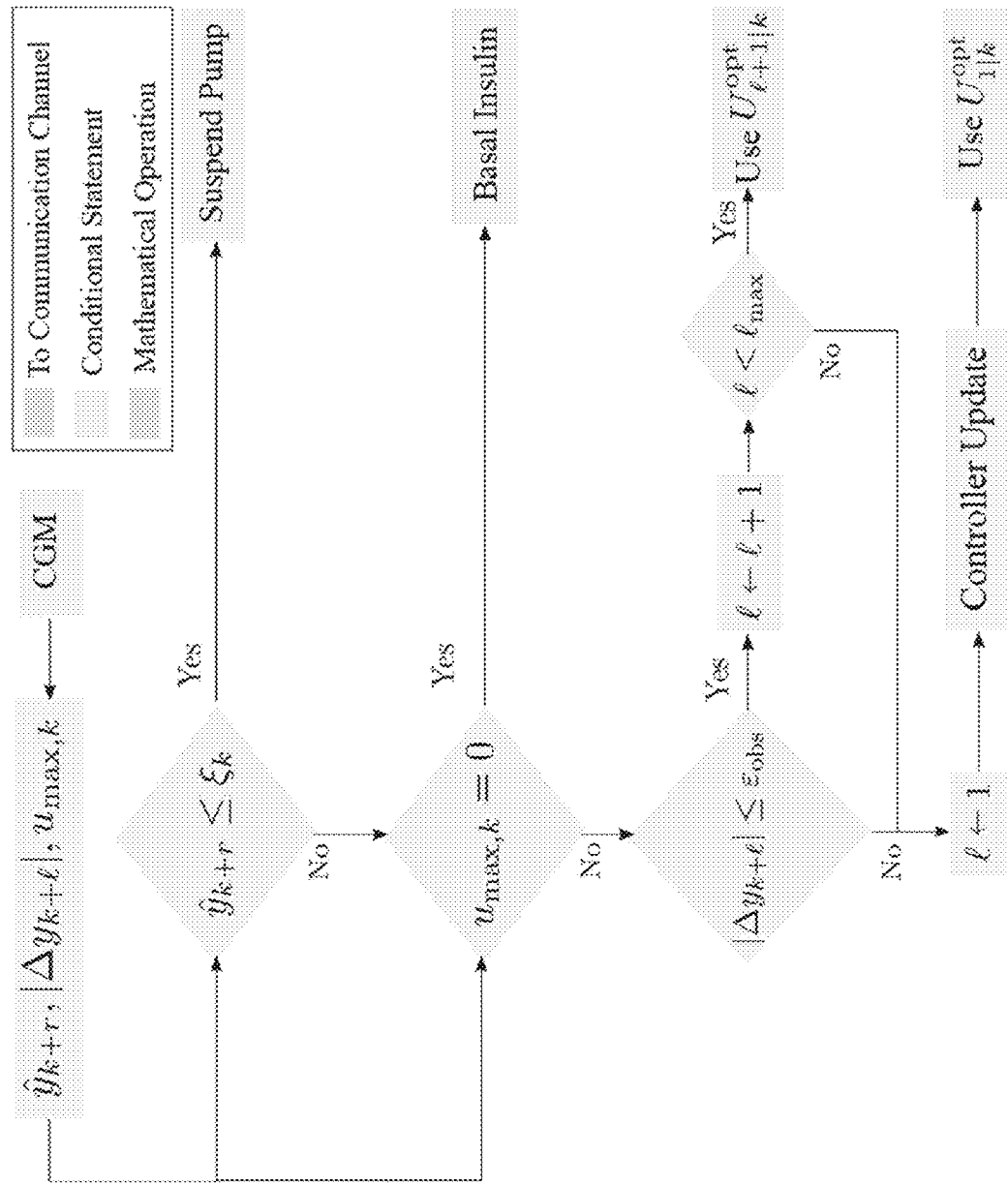
FIG. 1 is an example of a flowchart showing the logic for determining when to update the controller and describing conditions under which individual events are triggered.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Figure 9:
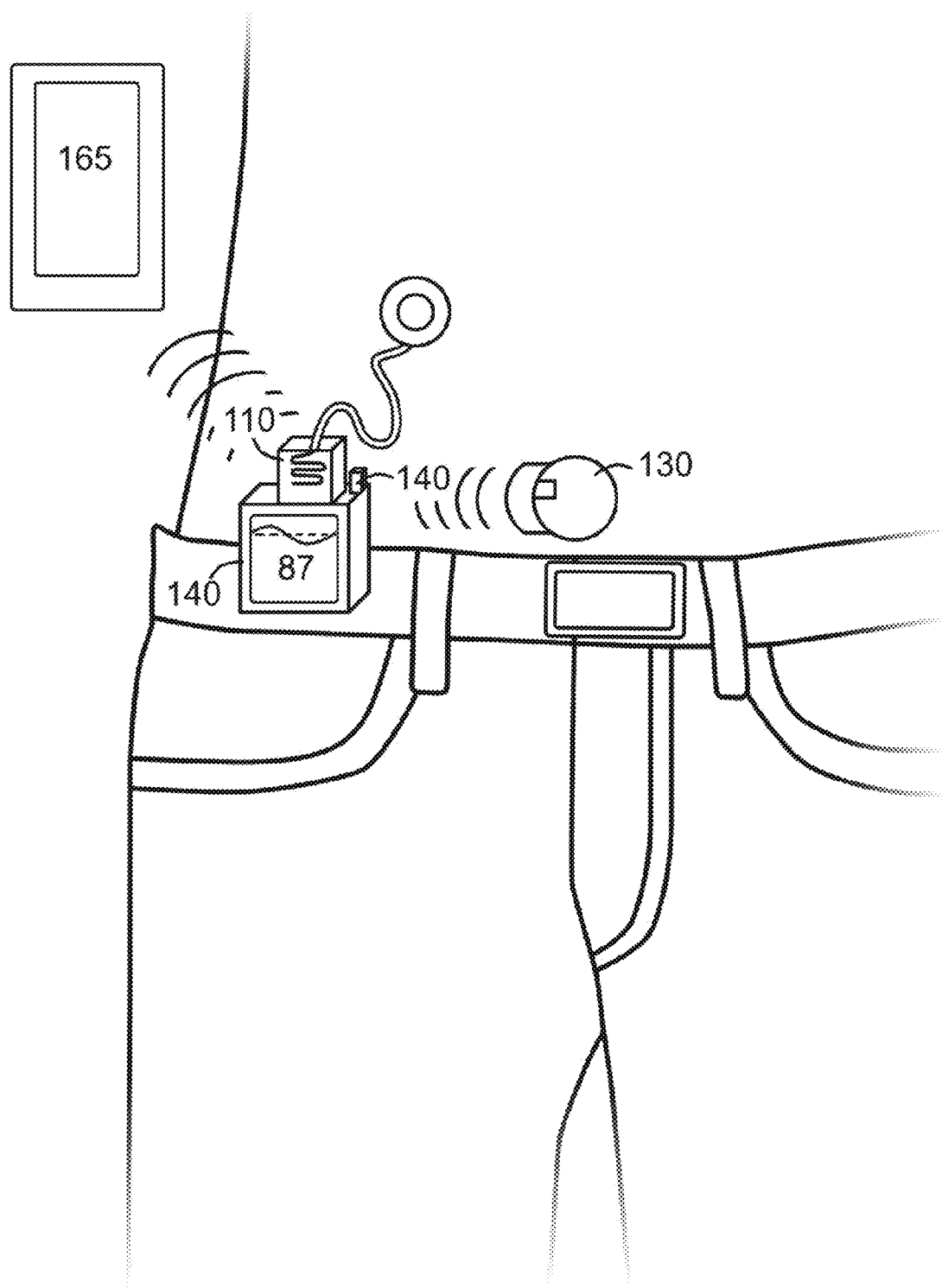
FIG. 9 is an example of an overview of an artificial pancreas system.

FIG. 9 illustrates an overview of an example artificial pancreas system. The artificial pancreas system includes a continuous glucose monitoring system (CGM) 140 for determining an amount of insulin to infuse, and an insulin infusion pump 110. A CGM 140 may provide a steady or periodic stream of information that reflects the patient's blood glucose levels. In some examples, a glucose sensor 130 may be placed under the patient's skin to measure the glucose in the fluid around the cells (interstitial fluid) which is associated with blood glucose levels. In other examples, other glucose sensors may be utilized. A small transmitter on the glucose sensor 130 may send information to a receiver 140. In some examples, a CGM 140 continuously displays and/or outputs glucose data that includes both an estimate of blood glucose levels of the patient and their direction and rate of change of these estimates.

In some examples, the CGM 140 may send the data to a mobile device 165 for display so the user can take action manually. For instance, a computed dose amount of insulin or glucagon could be relayed to the mobile device 165 for display to the user. In some examples, the mobile device 165 will display a notification or sound an alarm once receiving the instructions from the CGM 140.

A blood glucose device (BGD; such as a glucose meter) is used to calibrate the CGM 140. Currently, to get the most accurate estimates of blood glucose possible from a CGM 140, the patient needs to periodically calibrate the CGM 140 using a blood glucose measurement from a BGD; therefore, the BGD still plays a critical role in the proper management of patients with an APDS. However, over time, improved CGM 140 performance may eliminate the need for periodic blood glucose checks with a BGD.

An artificial pancreas 140 may not only monitor glucose levels in the body but may also automatically adjust the delivery of insulin by the insulin pump 110 to reduce high blood glucose levels (hyperglycemia) and minimize the incidence of low blood glucose (hypoglycemia) with little or no input from the patient.

The control system and memory of the CGM 140 may include logic functions or an algorithm running on the CGM 140 (or other component devices) that outputs control data packets with instructions for the insulin infusion pump 110. Sometimes, an artificial pancreas system is referred to as a "closed-loop" system, an "automated insulin delivery" system, or an "autonomous system for glycemic control."

A control model or control algorithm may be software embedded in an external or internal processor (controller) that receives information from the CGM and performs a series of processing steps based on glucose data received from the glucose sensor(s) 130. Based on these calculations, the controller sends dosing instructions to the infusion pump 110 or to the mobile device 165 for display. The control model can be run on the CGM or any other number of devices including an insulin pump 110, computer, mobile device 165. Based on the instructions sent by the controller, an infusion pump 110 adjusts the insulin delivery to patient.

Multiple effective approaches have been reported for implementing an Artificial Pancreas ("AP") on dedicated mobile platforms. For example, a control model or algorithm for bi-hormonal therapy that was clinically evaluated in an outpatient study of preadolescent children with T1DM [1] is implemented on an iPhone 4S. A model predictive control (MPC) algorithm implemented on a smartphone was evaluated in a hybrid-closed-loop clinical trial of adolescents with T1DM under free-living conditions [2]. Another smartphone implementation of a hybrid-closed-loop insulin delivery system was evaluated in a supervised outpatient study [3]. A pilot 'at-home' clinical study was conducted to evaluate the performance of a wearable device that integrates a Continuous Glucose Monitor (CGM), a Continuous Subcutaneous Insulin Infusion (CSII), a glucagon pump, the control algorithm and the wireless transmitters [4]. An AP system implemented on a miniature silicon microchip within a portable hand-held device is evaluated in [5]. The Medtronic hybrid closed-loop (HCL) system leverages a PID with insulin feedback (IFB) algorithm to automate basal insulin delivery while no meal is consumed. The Medtronic hybrid closed-loop (HCL) system incorporates the control algorithm into the insulin pump 110 and operates as a fully integrated system with the continuous glucose sensor 130. The safety and efficacy of this system was evaluated in several clinical studies [6], [7]. The disclosures of each of the articles referenced in this paragraph are hereby incorporated by reference in their entirety.

The development of artificial pancreas technology for deployment in low-energy, embedded devices is contingent upon selecting an efficient control algorithm for regulating glucose in people with type 1 diabetes mellitus (T1DM). The energy consumption of the AP can be lowered by reducing updates of the control model: the number of times the decision-making algorithm is invoked to compute an appropriate insulin dose. Physiological insights into glucose management are leveraged to design an event-triggered model predictive controller (MPC) that operates efficiently, without compromising patient safety.

Embedded/Wearable/Implantable Artificial Pancreas

Although the effectiveness of an automated artificial pancreas (AP) in the regulation of blood glucose in people with Type 1 Diabetes Mellitus (T1DM) is widely recognized, there is an imminent need to design embedded/wearable or implantable AP systems operating with low energy costs. Accordingly, in some examples the AP will be a miniaturized version of its components that is implantable in the human body and includes its own associated power source.

To this end, it is imperative to consider the factors involved in increasing the life expectancy of the device, since frequent alteration of hardware components such as the battery is undesirable, unsafe, and expensive. There are at least three main power drains on an embedded AP. First, there is the communication power for receiving CGM data and communicating with the pump and a display interface for user interaction, both of which are done via Bluetooth Low Energy in modern CGMs/pumps, thereby consumes low energy. Second is the idle power of the device as it is in sleep mode over most of the sampling time $\pi$ minutes. This can be minimized by optimized design of application-specific integrated circuits for the AP problem: that is, a prioritized design constraint could be to minimize idle current loss. Thirdly, the energy consumed by the processor. Although all three of these power ratings are extremely system dependent, a universal fact is that an MPC algorithm requires iterative solutions, and curtailing the number of iterations required implies that the time that the processor on is lower and thus, energy is saved.

Multiple control algorithms have been computationally and clinically evaluated for current AP systems, including: Proportional-Integral-Derivative (PID) [6], Fuzzy-Logic [8] and MPC [9]—[11] with a hardware-in-the-loop implementation in [12]. Of these strategies, MPC generates a high computational burden in spite of demonstrating excellent closed-loop clinical performance [13]. Low-complexity MPC algorithms such as explicit, multi-parametric, and embeddable variants of MPC are well-established; see [14]— [17]. A common feature that is revealed in MPC-based control in T1DM is that the number of controller updates can be reduced by observing, predicting, and exploiting future insulin-glucose dynamics.

Event Triggered Model Control

Accordingly, the inventors have developed an event-triggered MPC as an alternative to the standard MPC that computes optimal insulin doses at each time step (referred to as 'time-triggered' MPC). In event-triggered MPC, the sampling-period of the controller actions and the model used for predicting future glucose variations are rendered independent. That is, the optimal MPC action is computed only when specific events are triggered (or not triggered).

Figure 10:
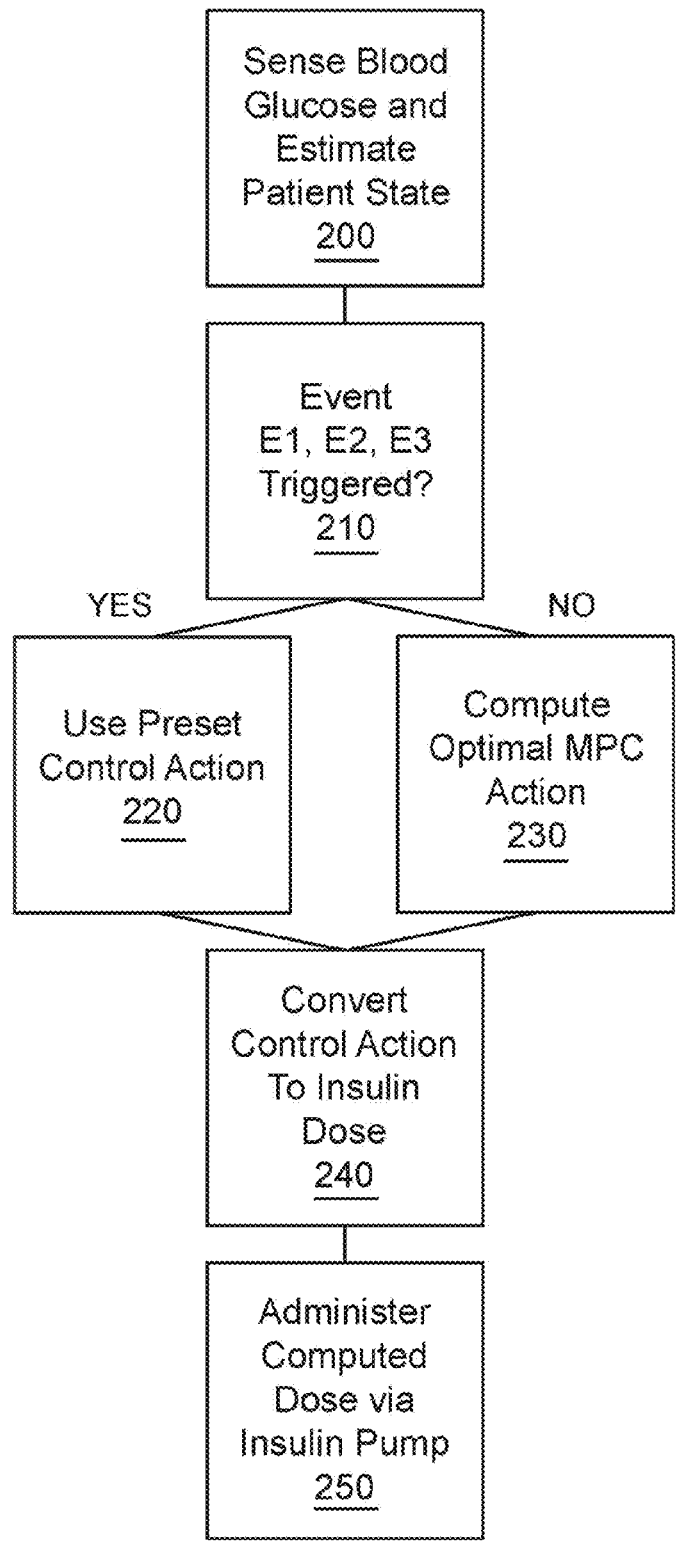
FIG. 10 is an example of a flowchart illustrating a process for event-based updating of a control algorithm for delivering insulin in an artificial pancreas.

FIG. 10 illustrates an example flow chart illustrating an example of an event triggering update to the control algorithm on the artificial pancreas. For instance, for the sensor 130 may sense the blood glucose 200 of the patient at various times. After each new measurement or after a combination of measurements, the control system (for instance on the MPC 140) may process the new measurement and determine whether an event is triggered 210 that requires updating the control model. If yes, then the control system may update the prediction model 220 to determine a new dose or set of doses of insulin 240 the insulin pump 110 will deliver to the patient 250. If no, then the current model 230 will be utilized to calculate the insulin doses 240 or the insulin doses already calculated will be utilized for delivery to the patient 250.

Accordingly, in some examples, the system may determine that a threshold is met that requires the system to deliver no more insulin, which may be determined at the step of determining whether an update event is triggered 210. Accordingly, for instance if the blood sugar is too low, the system may suspend operation of the pump to conserve power and energy. In other examples, other thresholds and frameworks may modify or augment this update model. In many cases, however, the system will not automatically use the full control model algorithm to determine a new dose at a set time interval—rather these processor intensive calculations will only be performed once an event is triggered based on a more basic calculation or evaluation of the blood glucose level reported by the glucose sensor 130 or other events as disclosed herein.

A multitude of event-based strategies have been reported in the literature for various applications. Event-triggering mechanisms include: the difference between the estimated state and the system state exceeding a specified threshold [19]—[21], violation of a Lyapunov function decay rate [22], and migrating between critical regions in linear MPC [23].

In some examples, an event-triggering method exploits physiological phenomena in conjunction with control-theoretic constructs to significantly lower the number of controller model updates and processor runtime, while respecting constraints arising from a clinical safety perspective. The proposed method is tested with rigorous hardware-in-the-loop simulation studies that constitute a pre-clinical assessment of the algorithm's safety and efficacy to be further evaluated in a clinical study setting. Accordingly, the benefits of this solution include: (1) it can be integrated with any variant of the MPC or other control algorithms for decision-making in the AP; (2) it significantly reduces processor runtime and energy consumption with good glycemic regulation performance in spite of large announced and unannounced meals.

Described herein is testing of an example event-triggered MPC, to evaluate its robustness to latent hypoglycemia, model mismatch and meal misinformation, with and without meal announcement, on the full version of the US-FDA accepted UVA/Padova metabolic simulator. In this example, the event-based controller remains on for 18 h of 41 h in closed-loop with unannounced meals, while maintaining glucose in 70-180 mg/dL for 25 h, compared to 27 h for a standard MPC controller. Additional features include: seamless integration with a wide variety of controllers reported in AP research; customized trade-off between glycemic regulation and efficacy according to prior design specifications; and, elimination of judicious selection of controller sampling times.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Model Predictive Control Framework for Artificial Pancreas

Following is an example of a model predictive control framework (MPC), specifically in an artificial pancreas application context.

A CGM sensor generally provides an estimate $y_k^{CGM}$ of the subject's blood glucose (BG) concentration. In order to regulate the BG, predictive control strategies employ models possessing the general form $$x_{k+1} = f(x_k, u_k^{act}) \quad (1a)$$

$$y_k = h(x_k) \quad (1b)$$

k denotes the time index, $x_k \in \mathbb{R}^n$ denotes the patient state, and the scalar $y_k$ denotes an estimate of $y_k^{BG}$ computed via a measurement model. Let $\tau$ denote the sampling-period of the system; then the scalar $u_k^{act}$ denotes the actual insulin infusion rate in units (U) per t minutes. This actual insulin infusion rate has two components: $u_k^{act} = u_k + u_k^*$, where $u_k$ is the control action (deviation from basal), and $u_k^*$ denotes the time-varying but subject-specific basal insulin infusion rate. General nonlinear functions f and h are presented in the predictive model formulation (1); these subsume widely used insulin-glucose models such as linear discrete-time models [25], nonlinear models [26], [27], and input-output autoregressive models [28].

The standard implementation of an MPC is via state-feedback. Therefore, it is necessary to design an estimator to procure the state $x_k$ of the system (1) based on the current CGM value $y_k^{CGM}$, or other available information at time k (for example: previous control actions, CGM measurements, estimated glucose values). Popular estimation algorithms in the AP literature include: linear observers [29], moving horizon estimators [30], [31], or Kalman filters [32], [33].

Let $N_y$ and $N_u$ be the prediction and control horizon of the MPC, respectively. Let $$U_{1:N_u|k} \triangleq \{u_{k+1}, \ldots, u_{k+N_u}\}$$

denote a sequence of control actions, or amounts of insulin to be delivered 250 by the insulin pump 110 from time step k+1 to k+$N_u$. For any pair of integers a, b satisfying a<b, suppose $\mathbb{Z}_a^b \triangleq \{a, a+1, \ldots, b-1, b\}$. Then the optimal MPC control sequence is computed by solving $$U_{1:N_u|k}^{opt} = \underset{U_{1:N_u|k}}{\mathrm{argmin}} J$$

Subject to:

$$0 \leq \bar{u}_r + u_r^* \leq u_{max,k} \forall r \in \mathbb{Z}_1^{N_u}$$

$$\bar{u}_r \leq u_{max,k}^{IOB} \forall r \in \mathbb{Z}_1^{N_u}$$

$$\bar{x}_r = f(\bar{x}_{r-1}, \bar{u}_r + u_r^*) \forall r \in \mathbb{Z}_1^{N_u}$$

$$\bar{y}_r = h(\bar{x}_r) \forall r \in \mathbb{Z}_1^{N_u}$$

$$\bar{x}_0 = x_k \forall r \in \mathbb{Z}_1^{N_u} \quad (2)$$

where J is a cost function designed for glycemic regulation, and $\bar{x}$, $\bar{u}$ are artificial variables used to denote open-loop state predictions and control actions (deviations from basal), respectively. An additional constraint on the insulin output is the insulin-on-board (IOB) upper bound, denoted $u_{max,k}^{IOB}$. The IOB, described in [34], accounts for the administered insulin history and computes the remaining active insulin in the body based on clearance rates in the human endocrine system. In addition to a positivity constraint (the drug infusion rate $u_k^{act}$ cannot be negative), the control action must also satisfy a time-varying upper bound $u_{max,k}$.

The framework in (2) subsumes commonly used MPC methods such as set-point MPC [35], adaptive set-point MPC [36], zone MPC [37], periodic zone MPC [29], and other MPC variants such as those reported in [32], [38], [39].

The quantity $u_{max,k}^{IOB}$ indicates how much insulin above the basal insulin rate $u_k^*$ can be administered safely (from a clinical perspective) at the current time step k.

Widely used $u_{max,k}$ include mechanical constraints such as the maximum infusion rate of the pump, physiological constraints such as the insulin-on-board constraint, and safety constraints such as limitations on insulin infusion post-exercise, limits on glucose and insulin velocity; see [34], [40], [41].

It is standard practice in time-triggered MPC to implement only the first element $U_{1|k}^{opt}$ of the sequence $U_{1:N_u|k}^{opt}$, and discard the tail $U_{2:N_u|k}^{opt}$. However, examples are provided below that utilized the information contained in the tail of the control sequence. Accordingly, if the information is implemented carefully, the tail provides an avenue for reducing the number of controller updates required, and therefore enhancing the efficacy of the design.

Event Triggered—Model Predictive Control Framework for an Artificial Pancreas

While above is the framework for a time triggered MPC, the inventors have developed an event-triggered MPC that is useful to reduce the number of updates made to the MPC overall. Note that these event-triggers can be integrated with many widely-used MPC variants, or other control algorithms that leverage design models characterized in the form (1) for predicting future system behavior.

Example 1: Predictive Pump Suspension

The highest priority in terms of clinical safety is to prevent sustained hypoglycemia (BG<70 mg/dL). To this end, pump suspension algorithms such as low-glucose predictors have been devised in, for example [42]. In this paper, we employ a linear predictor to estimate the BG level r∈N samples into the future, that is, $$\hat{y}_{k+r} = y_k^{CGM} + (y_k^{CGM} - y_{k-1}^{CGM})r.$$

When the predicted BG level $\hat{y}_{k+r}$ is dangerously low, the pump 110 may be suspended, or the control system may not send a pump signal to the pump 110 until the BG levels return to the clinically safe region of 70-180 mg/dL. This event can be written as:

$$E_1: \text{if } \hat{y}_{k+r} \leq \xi_k \text{ then } u_k \leftarrow -u_k^*,$$

Where $\xi_k \in \mathbb{R}$ is a design variable that enables the clinician or user to customize the predicted BG level below which they wish to suspend the pump; the dependence on the time step k implies that this variable can be altered when necessary. For example, users apprehensive of nocturnal hypoglycemia can raise the value of $\xi_k$ to enforce early pump suspension.

If the conditions for suspension of the pump 110 are met, the control module need not be switched on, since the appropriate control action is $u_k^{act}=0$. In some examples, the system will use a linear predictor to predict future BG values instead of a design model (1).

This is primarily to reduce computational effort, since this conditional statement is checked each time a new CGM value is available to determine whether to suspend the pump 110. To prevent frequent pump suspension due to inaccuracies inherent to linear extrapolation, the design parameter r is selected to be a small integer.

Example 2: Exploiting Insulin-On-Board Constraints to Reduce Computations

If the predicted CGM value does not warrant suspension, an event-triggering variable may be utilized that could be denoted $u_{max,k}^{IOB}$, that indicates the IOB upper bound. From a physiological perspective, when $u_{max,k}^{IOB}=0$ (or, the upper bound of insulin is not at a maximum), and the predicted glucose trajectory is not low, the system can safely infuse basal insulin without invoking the MPC law. Accordingly, the following condition can be formulated:

$$E_2: \text{if } u_{max,k}^{IOB}=0 \text{ then } u_k \leftarrow 0,$$

If the previous two events (pump suspension and $u_{max,k}^{IOB}$ saturation) are not triggered, the control system may cause the following event-triggered variant of the MPC.

Example 3: Using the Tail of the Control Sequence

Recall that the control horizon of the MPC is denoted by $N_u$, and that $\tau$ signifies the sample-period of the system. The output estimation error may be defined as:

$$\Delta y_k \triangleq y_k^{CGM} - y_k. \quad (3)$$

This is the difference between the CGM value and the estimated BG value at time step k.

Solving (2) results in the computation of an optimal MPC sequence $U_{1:N_u|k}^{opt}$ at time k. This sequence contains a series of control actions or insulin delivery doses 250. Instead of implementing only the first control action $U_{1|k}^{opt}$, in this event-triggering step, the system may apply the control actions in the tail of the control sequence $U_{2:N_u|k}^{opt}$ until either:
  (i) events E1 or E2 are triggered;
  (ii) the output estimation error norm $|\Delta y_k|$ exceeds a pre-specified threshold $\varepsilon_{obs}$; or,
  (iii) the first $l_{max}$ control actions in $U_{1:N_u|k}^{opt}$ are implemented.

Note that the exploitation of the tail of the control based on output estimation errors is adapted from [19]. The tail of the control sequence is applied only if the estimated BG and actual CGM values are in close proximity. If this happens, the open-loop BG predictions are likely to be sufficiently accurate estimates of the actual BG values.

This condition is written as:

$$\left.\begin{array}{l} !E_1 \\ \text{and} \\ !E_2 \\ E_3: \text{if and} \\ \|\Delta y_k + \ell\| \leq \varepsilon_{obs} \\ \text{and} \\ \ell < \ell\text{max} \end{array}\right\} \text{then } u_{k+\ell} \leftarrow \underbrace{U_{\ell+1|k}^{opt}}_{tail},$$

where l denotes a counter initialized at one.

The selection of $\varepsilon_{obs}$ is inextricably linked to the regulatory performance of the controller. If $\varepsilon_{obs}$ is large, the solution for the optimal MPC trajectory is not triggered until the estimation error $\Delta y_k$ is large, which may result in larger variability of BG values during glycemic regulation. The advantage of larger $\varepsilon_{obs}$ is that the microprocessor is operated less often, as the system can rely on the stored tail of the control sequence to administer future insulin doses. Conversely, a small $\varepsilon_{obs}$ results in tighter control but more frequent controller updates. Note that choosing $\varepsilon_{obs}=0$ generalizes to the standard time-triggered approach with pump suspension.

The design parameter $l_{max}$ signifies at most how many control actions in the tail $U_{2:N_u|k}^{opt}$ could be actuated before recomputing an optimal MPC action trajectory (assuming that E1 and E2 have not triggered). The relation between $l_{max}$ and the regulatory performance of the MPC is similar to $\varepsilon_{obs}$: namely, if $l_{max}$ is small, the energy drain is large, but the control performance is tighter. Without a highly accurate model of the insulin-glucose dynamics, a large $l_{max}$ (at most Nu) is expected to result in controller performance degradation.

If none of the conditions E1, E2 and E3 are satisfied, the control module is switched on and the optimization problem (2) is solved. That is, $$\text{if } !E_1 \text{ and } !E_2 \text{ and } !E_3 \text{ then } u_k \leftarrow U_{1|k}^{opt}.$$

FIG. 1 illustrates an example of a flow chart illustrating the logic that may be implemented by a control system that will send instructions to an insulin pump 110.

Accordingly, each time the control system needs to update the control model, the solution and associated control actions, $U_{1:N_u|k}^{opt}$ may be stored in the systems memory (e.g. flash memory) each time the optimization problem (2) is solved. The tail of the control sequence (e.g. the remaining control actions that could be implemented to operate the insulin pump 110) can therefore be subsequently withdrawn from the memory, rather than re-solving the optimization problem at each time-step. This is expected to result in longer idle times of the control system, e.g. MPC control module, and less frequent controller updates than the time-triggered version, especially in the absence of sudden glucose variations, such as those arising due to meals or exercise.

From an embedded implementation perspective, a concern is that packets are dropped during CGM or pump transmissions. Therefore, it is critical to build robustness around the control algorithm. In case of multiple missing CGM measurements or if communication with the pump or CGM is not established within a predefined time, we switch the AP to open-loop mode or infuse basal insulin for safety.

Example 4: Prioritization of Events for Safe Glycemic Regulation

Following are illustrations of prioritization of the event triggered scenarios.

In many examples, suspension may have higher priority than the MPC. For instance, if the MPC has higher priority than the pump suspension, then, at low estimated BG levels it tends to be unlikely that control action other than suspension is useful, and thus it is generally wasteful to invoke expensive computations. Furthermore, even in cases where a non-suspension would be useful, for example, when BG is low and rising quickly, a suspension that is continued a short time longer than had MPC been invoked is not significantly deleterious to subjects' health. Thus, this rule is computationally cost effective and safe.

Accordingly, event E1 (suspension) may have a higher priority than E2 for the following reasons. Recall that $u_k$ denotes the insulin infusion recommended above the basal rate. Hence, $u_k=0$ implies that the actual infusion is the basal, $u^*$. When $u_{max,k}^{IOB}=0$, event E2 will be triggered and basal insulin will be supplied instead of computing optimal MPC actions. If E1 has lower priority than E2, then one could be supplying basal insulin even if the optimal MPC action $u_k<0$, which would result in controller-induced hypoglycemia. To avoid this, the system predictively suspends the pump, making E1 higher priority.

Example 5: Case Study: Event-Triggered Periodic Zone Model Predictive Control Following is an overview of the zone MPC (ZMPC) formulation proposed in [37], and the improved periodic zone MPC framework reported in [29]. The objective of this section is to illustrate how an event-triggering methodology integrates seamlessly with the periodic ZMPC.

A. Insulin-Glucose Model

A 3-dimensional linear discrete-time model, proposed in [25], is used as a design model. The model has a sampling time $\tau=5$ min. It is important to note that the model is linearized around a steady-state glucose value of $y^*=110$ mg/dL with a time-varying basal insulin rate $u_k^*$ personalized with respect to each subject with T1DM via the insulin to carbohydrate ratio, total daily insulin amount, and basal insulin profile. This model has clinically validated in [29], [43] and has demonstrated accurate predictive behavior. The transfer function representation of the measurement output y and the control input u is given by $$G(z^{-1}) = \frac{1800Fc}{u_{TDI}} \frac{z^{-3}}{(1-p_1 z^{-1})(1-p_2 z^{-1})^2}, \quad (4)$$

where $z-1$ is the backward shift operator, $p_1=0.98$ and $p_2=0.95$ are the poles, $F=1.5$ is a safety factor determined by clinicians, $u_{TDI}$ denotes an admissible subject-specific total daily insulin amount, and $c:=-60(1-p_1)(1-p_2)^2$ is a constant required for unit conversion, whose units depends on the units used in data for the design of the poles of the model.

The state-space representation of the discrete-time transfer function model (4) has the form $$x_{k+1}=Ax_k+Bu_k \quad (5a)$$

$$Y_k=Cx_k, \quad (5b)$$

where k denotes the discrete time index, $x_k$ is the subject state at the kth time instant, $u_k$ is the control action, and $y_k$ is the output of the design model, with matrices $$A = \begin{bmatrix} p_1+2p_2 & -2p_1p_2-p_2^2 & p_1p_2^2 \\ 1 & 0 & 0 \\ 0 & 1 & 0 \end{bmatrix},$$

$$B = \frac{180Fc}{u_{TDI}}[1 \; 0 \; 0]^T,$$

and $C=[0 \; 0 \; 1]$. Clearly, this model conforms to the representation (1) with $f:=Ax+Bu$ and $h:=Cx$.

The state $x_k$ of the system (5) is computed based on the current CGM value $y_k^{CGM}$ using a linear observer of the form $$x_k=\hat{x}_k+L((y_k^{CGM}-y^*)-C\hat{x}_k) \quad (6)$$

where L is the observer gain matrix, and $$\hat{x}_k \triangleq Ax_{k-1}+Bu_{k-1}$$

is an estimate of the current state based on the previously estimated state $x_{k-1}$ and the (known) previous control action $u_{k-1}$.

B. Constraints for Safe Glucose Variation

The control objective is to regulate the subject's glucose level $y_k^{act}$ to within a time-dependent periodic zone of safe glucose values. As hypothesized in [24] and clinically validated in [29], [43], employing a periodic zone as a glucose target rather than a fixed set point offers various clinical advantages such as reduction of nocturnal hypoglycemic events due to conservative infusion of insulin. Furthermore, the ZMPC leads to reduced actuation; our proposed event-triggering algorithm further reduces the actuation via prioritized, event-based conditional constructs.

A periodic zone is represented mathematically as $$y_k^{low} \leq y_k^{CGM} \leq y_k^{high},$$

where the lower and upper bounds are given by $$y_k^{low} = \begin{cases} y_{night}^{low} & \text{from 12 AM to 5 AM,} \\ \psi(y_{night}^{low}, y_{day}^{low}) & \text{from 5 AM to 7 AM,} \\ y_{day}^{low} & \text{from 7 AM to 10 PM,} \\ \psi(y_{day}^{low}, y_{night}^{low}) & \text{from 10 PM to 12 AM,} \end{cases} \quad (8a)$$

and $$y_k^{high} = \begin{cases} y_{night}^{high} & \text{from 12 AM to 5 AM,} \\ \psi(y_{night}^{high}, y_{day}^{high}) & \text{from 5 AM to 7 AM,} \\ y_{day}^{high} & \text{from 7 AM to 10 PM,} \\ \psi(y_{day}^{high}, y_{night}^{high}) & \text{from 10 PM to 12 AM,} \end{cases} \quad (8b)$$

respectively. For $a, b \in \mathbb{R}$, the map $\psi(a, b)$ denotes a smooth transition between a and b; in this work, one can choose $\psi$ to be a cosine function. The positive scalars $y_{day}^{high}$, $y_{night}^{high}$, $y_{day}^{low}$, and $y_{night}^{low}$ night are design parameters which are determined after discussion with endocrinologists.

If the designer wishes to implement a fixed target glucose level (commonly referred to as a set-point MPC), this can be modeled as a zone with identical upper and lower bounds, that is, when $y_{day}^{high}=y_{night}^{high}=y_{day}^{low}=y_{night}^{low}$.

C. Constraints for Safe Insulin Delivery

The control action $u_k$ must also respect an upper bound that takes into account the administered insulin history and computes the remaining active insulin in the body based on clearance rates in the human endocrine system. This is commonly referred to as the insulin-on-board (IOB) upper bound [34]. The active insulin content can then be leveraged to formulate a constraint (the IOB constraint) to restrict the allowable magnitude of insulin infused, thereby preventing an overdose.

Empirical clinically-validated insulin action curves are used to compute the current IOB value. These discretized curves are sampled every τ min and represent the fraction of insulin that remains active after 2, 4, 6 and 8 hours. One can denote these curves by $\Theta_{lhr} \in$ $$\mathbb{R}^{\frac{8}{\tau} \cdot 60},$$

where $l \in \{2, 4, 6, 8\}$. In order to estimate the current IOB value, one can first select the correct IOB curve based on the current CGM value $u_k^{act}$.

and the following heuristic:

$$\Theta_k := \begin{cases} \Theta_{2hr}, & \text{if } y_k^{CGM} > 300 \text{ mg/dL}, \\ \Theta_{4hr}, & \text{if } y_k^{CGM} \in (200, 300] \text{ mg/dL}, \\ \Theta_{6hr}, & \text{if } y_k^{CGM} \in (140, 200] \text{ mg/dL}, \\ \Theta_{8hr}, & \text{otherwise}. \end{cases} \quad (9)$$

Let $U_{k-95:k} \in \mathbb{R}^{96}$ and $U_{k-95:k}^{meal} \in \mathbb{R}^{96}$ denote the vector of insulin infusions and meal-induced manual insulin boluses administered over the past 8 hours, respectively. Then the estimated current IOB value is given by $$IOB_k \triangleq \Theta_k^T U_{k-95:k} + \Theta_{4hr}^T U_{k-95:k}^{meal}$$

With an estimate of the current IOB, we compute the IOB upper bound as:

$$u_{max,k}^{IOB} \triangleq \max\left\{0, \frac{y_k^{CGM} - y^*}{C_f} - IOB_k\right\}, \quad (10)$$

where $C_f[(\text{mg/dL})/U]$ is a patient-specific clinical parameter, called the 'correction factor'. With the above constraints, we are now ready to formulate the optimization problem that yields appropriate insulin doses for safe glycemic regulation.

D. Computing Insulin Doses

An important ingredient required for the optimization for-mutation is the so-called 'zone-excursion function'.

$$Z(y_k) = \begin{cases} (y_k + y^*) - y_k^{high} & \text{if } y_k + y^* > y_k^{high}, \\ y_k^{low} - (y_k + y^*) & \text{if } y_k + y^* < y_k^{low}, \\ 0 & \text{otherwise}, \end{cases}$$

where $y_k^{low}$ and $y_k^{high}$ have been previously defined in (8).

Let Ny and Nu denote the prediction and control horizon of the ZMPC, and let $U_{1:N_u|k}$ denote a sequence of control actions from time step k+1 to k+Nu. Then the optimal control sequence is computed by solving $$U_{1:N_u|k}^{opt} = \underset{U_{1:N_u|k}}{\operatorname{argmin}} \left[ \sum_{r=0}^{N_y-1} Qz_r^2 + \check{R}\hat{u}_r^2 + \check{R}\check{u}_r^2 \right] \quad (11)$$

subject to:

$x_{r+1} = Ax_r + Bu_r, \forall 0, \ldots, N_y-1$ $y_r = Cx_r, \forall 0, \ldots, N_y-1$ $x_0 = x_k$ $z_r = \mathcal{Z}(y_r), \forall 0, \ldots, N_y-1$ $\hat{u}_r = \max\{0, u_r\}, \forall 0, \ldots, N_u-1$ $\check{u}_r = \min\{0, u_r\}, \forall 0, \ldots, N_u-1$ $u_r = \hat{u}_r + \check{u}_r, \forall 0, \ldots, N_u-1$ $u_r = 0 \forall N_u, \ldots, N_y-1$ $-u_r^* \leq u_r \leq \min\{u_{max,k}^{IOB}, u_{max}^{pump}\} - u_r^*, \forall 0, \ldots, N_u-1$.

Although one can compute the optimal ZMPC control sequence $U_{1:N_u|k}^{opt}$, one can only apply the first action $U_{1:k}^{opt}$ of the sequence.

Since this optimized control action is derived with respect to the linearized model, the actual insulin dose administered is given by $u_k^{act} = U_{1:k}^{opt} + u_k^*$.

E. Event-Triggered ZMPC Parameters for Simulation

Parameters for the ZMPC have been clinically validated in [29], [43]. The system may select a predictive horizon of Ny=9 (45 min), and control horizon Nu=5 (25 min) for the ZMPC. The periodic zone is parameterized by $y_{night}^{low}=100$ mg/dL, $y_{day}^{low}=80$ mg/dL, and $y_{night}^{high}=u_{day}^{high}=140$ mg/dL. The weights are selected as Q=1, $\check{R}$=7000 and $\check{R}$=100.

For the event E1, the linear predictor horizon is chosen to be r=5 samples (25 min), and the pump suspend threshold $\xi_k$ is selected to be 80 mg/dL in the morning (7 AM-11 PM), and raised to 100 mg/dL at night (11 PM-7 AM) to prevent nocturnal hypoglycemia. For event E2, one can compute $u_{max,k}^{IOB}$ as in (10). For E3, one can have a choice of $1 \leq l_{max} \leq N_u$. One may choose lmax=3 because the linear model (5) typically stabilizes to the zone $[y_k^{low}, y_k^{high}]$ within three samples, and the rest of the control trajectory degrades to the basal insulin rate $u_k^*$.

Another design parameter for E3 is $\varepsilon_{obs}$, this scalar is strongly correlated with the trade-off between regulatory performance and controller update frequency. Thus, in the following section, this example investigates the efficiency and regulatory performance trade-off with multiple. To select a range for $\varepsilon_{obs}$, we leverage clinical data obtained from 17 patients in [13]. The histogram of clinical variability given in FIG. 7 has a median of 3 mg/dL and an interquartile range of 1 to 6 mg/dL. For reasons that will be made clear in the sequel, the truncated range of 1 to 3 mg/dL is selected.

Example 6: Stimulation on 111 Subjects

Following is a description of a simulation of the disclosed systems and methods on 111 subjects, including the hardware platform, and results of the simulation study. The 111 subjects included 100 from the full version of the FDA-accepted UVA/Padova simulator [44], 10 from the academic available version of the simulator, and a subject constructed by averaging the parameters of the 110 other subjects. The study began by testing the performance of the event-triggered ZMPC (ET-ZMPC) with multiple $\varepsilon_{obs}$ both with and without meal announcement to determine a satisfactory value. Fixing this value of Lobs, one can verify the robustness of the ET-ZMPC with respect to incorrect basal infusion rates and erroneously estimated carbohydrate levels in announced meals.

Figure 2:
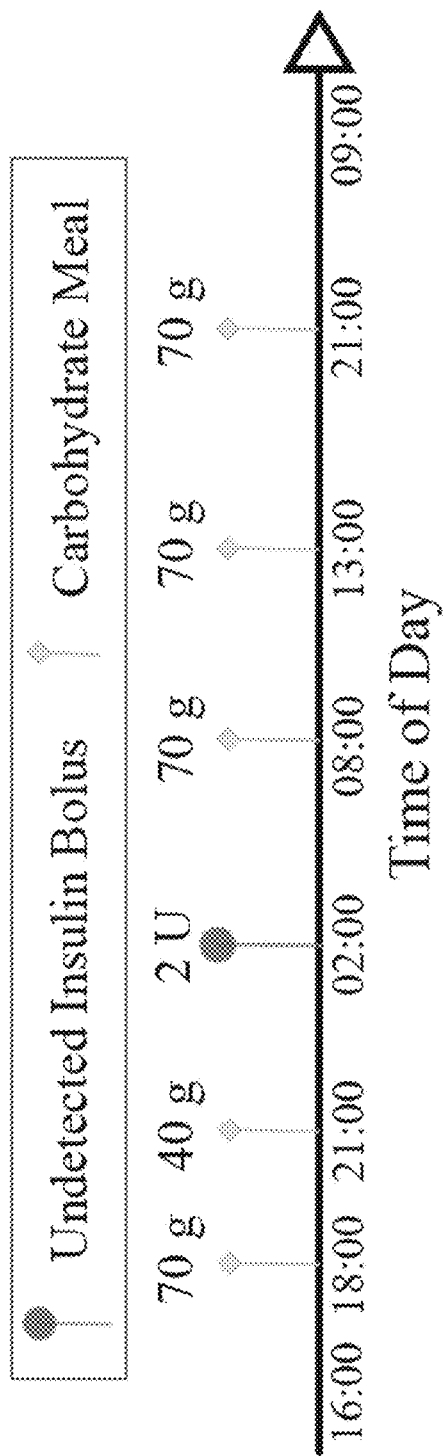
FIG. 2 is an example of a meal protocol with multiple meal challenges and an undetected insulin bolus.

FIG. 2 Illustrates a scenario for testing the performance of the proposed event-triggered AP. The closed-loop starts at 4 PM the first day. Two meals are consumed the first day followed by a simulated secret insulin bolus to force a nocturnal hypoglycemic event. The second day includes a meal plan of three meals with long intervals between meals. The closed-loop ends the next day at 9 AM.

A. Clinical Scenario and Challenges

The clinical scenario used to test the proposed controller is presented in FIG. 2. Five meals in total are consumed within 41 simulated hours of closed-loop control. A 70 g meal of carbohydrates is consumed at 6 PM, after 2 hours of closed-loop initiation, followed by a snack of 40 g of carbohydrates at 9 PM. The system is challenged at 2 AM with an undetected insulin bolus to represent a sudden, nocturnal hypoglycemic episode that is a major concern for patients with T1DM. The following morning, a 70 g breakfast is provided at 8 AM, a 70 g lunch at 1 PM, and a dinner of 70 g of carbohydrates at 9 PM. Two cases are considered to evaluate the performance of the ET-ZMPC algorithm;
  (i) all meals are unannounced and the controller is responsible for computing appropriate insulin doses in a completely automated manner; and,
  (ii) all meals are announced and a manual insulin bolus is administered based on a patient-specific carbohydrate/insulin ratio; the controller is expected to regulate the basal insulin satisfactorily in the pre- and post-prandial time ranges.

The challenge for the event-based controller is to perform comparably to the time-triggered ZMPC (TT-ZMPC), in a safe manner, with fewer controller updates. The safety of the event-triggering mechanism is tested by assessing its ability to prevent severe nocturnal hypoglycemia induced by an undetected insulin bolus (representing manual overbolusing, latent exercise effects, or heightened insulin sensitivity due to collateral illness) of 2 U magnitude at 2 AM on the first night.

B. Hardware-In-the-Loop-Simulation Studies

The periodic ZMPC control action sequences, observer, IOB computation, and the event-triggering mechanism are deployed on a single-board computer known as Raspberry Pi 3 Model B*. A 32 GB microSD card is used as the flash memory of the entire system. The board contains a 64-bit quad-core ARMv8 central processing unit (CPU) that operates on up to 1.2 GHz clock speed. The Raspberry Pi emulates an embedded AP: it communicates with MATLAB via Ethernet to receive virtual CGM data from the Simulator and wirelessly transmits the computed control action back to the Simulator. All code for the Raspberry Pi is written in Python 2.7 and the quadratic programming problem inherent to the MPC is solved using the CVXOPT toolbox [45]. The rationale behind deploying the AP as an embedded system is to collect realistic power numbers and demonstrate the feasibility of implementing the event-based ZMPC algorithm on a miniaturized device. An overview of the hardware-in-the-loop (HIL) simulation protocol and the components used therein is provided in FIG. 3.

*https://www.raspberrypi.org/

Table I below shows controller performance compared with announced and unannounced carbohydrate meals (mean±one standard deviation) for 111 subjects. The grey shading is used to depict overnight metrics. The '*' implies a p-value<0.05 and '**' indicates a p-value<0.001.

TABLE I

| PERFORMANCE METRICS | STANDARD TT-ZMPC | PROPOSED ET-ZMPC | | |
|---|---|---|---|---|
| | | $\varepsilon_{obs} = 1$ | $\varepsilon_{obs} = 2$ | $\varepsilon_{obs} = 3$ |
| [A] UNANNOUNCED MEALS | | | | |
| Overall BG <70 mg/dL [%] | 1.64 ± 2.85 | 1.27 ± 2.09 | 1.15 ± 1.99 | 1.07 ± 1.84 |
| Overall BG in 70-180 mg/dL [%] | 66.00 ± 8.63 | 63.72 ± 8.81 (*) | 61.09 ± 8.87 (*) | 58.73 ± 8.85 (*) |
| Overall BG >180 mg/dL [%] | 31.90 ± 8.64 | 34.51 ± 9.08 (*) | 37.27 ± 9.37 (*) | 39.80 ± 9.45 (*) |
| Overall BGmedian [mg/dL] | 141.95 ± 13.47 | 146.94 ± 15.99 (*) | 152.52 ± 18.92 (*) | 157.81 ± 21.40 (*) |
| Overall Percent Controller Updates [%] | 100.00 ± 0.00 | 59.34 ± 6.86 () | 47.58 ± 5.73 () | 38.83 ± 4.58 (**) |
| Overall Energy Consumed [mAh] | 4.79 ± 0.32 | 2.86 ± 0.33 () | 2.28 ± 0.29 () | 1.87 ± 0.23 (**) |
| Overnight BG <70 mg/dL [%] | 3.24 ± 5.29 | 2.71 ± 4.35 | 2.46 ± 4.24 | 2.45 ± 4.23 |
| Overnight BG in 70-180 mg/dL [%] | 88.24 ± 8.51 | 86.56 ± 8.86 | 84.37 ± 9.50 (*) | 81.93 ± 9.94 (*) |
| Overnight BG >180 mg/dL [%] | 8.16 ± 6.55 | 10.36 ± 8.03 (*) | 12.75 ± 9.42 (*) | 15.22 ± 10.25 (*) |
| Overnight BGmedian [mg/dL] | 121.61 ± 8.53 | 123.93 ± 8.96 (*) | 126.39 ± 10.41 (*) | 129.12 ± 11.85 (*) |
| Overnight Percent Controller Updates [%] | 100.00 ± 0.00 | 48.02 ± 11.05 () | 37.48 ± 9.11 () | 30.17 ± 7.13 (**) |
| Overnight Energy Consumed [mAh] | 5.07 ± 0.43 | 2.43 ± 0.56 () | 1.88 ± 0.45 () | 1.53 ± 0.37 (**) |

TABLE I-continued

| PERFORMANCE METRICS | STANDARD TT-ZMPC | PROPOSED ET-ZMPC | | |
|---|---|---|---|---|
| | | $\varepsilon_{obs} = 1$ | $\varepsilon_{obs} = 2$ | $\varepsilon_{obs} = 3$ |
| [B] ANNOUNCED MEALS | | | | |
| Overall BG <70 mg/dL [%] | 0.76 ± 1.46 | 0.96 ± 1.66 | 0.85 ± 1.52 | 0.80 ± 1.49 |
| Overall BG in 70-180 mg/dL [%] | 86.65 ± 9.73 | 86.75 ± 10.26 | 86.38 ± 10.35 | 86.07 ± 10.79 |
| Overall BG >180 mg/dL [%] | 12.60 ± 9.08 | 12.29 ± 9.71 | 12.77 ± 10.01 | 13.14 ± 10.49 |
| Overall BG median [mg/dL] | 130.40 ± 7.43 | 129.99 ± 9.10 | 130.89 ± 10.01 | 131.30 ± 10.97 |
| Overall Percent Controller Updates [%] | 100.00 ± 0.00 | 33.04 ± 10.16 () | 25.88 ± 8.26 () | 20.68 ± 6.92 (**) |
| Overall Energy Consumed [mAh] | 5.09 ± 0.30 | 1.70 ± 0.49 () | 1.34 ± 0.40 () | 1.07 ± 0.33 (**) |
| Overnight BG <70 mg/dL [%] | 1.67 ± 3.17 | 1.79 ± 3.23 | 1.54 ± 2.94 | 1.50 ± 3.05 |
| Overnight BG in 70-180 mg/dL [%] | 96.63 ± 5.43 | 96.22 ± 5.86 | 96.29 ± 5.68 | 96.22 ± 5.76 |
| Overnight BG >180 mg/dL [%] | 1.50 ± 3.01 | 1.77 ± 3.77 | 1.89 ± 3.93 | 2.03 ± 4.13 |
| Overnight BGmedian [mg/dL] | 119.88 ± 7.75 | 119.41 ± 8.75 | 119.81 ± 9.37 | 120.10 ± 10.02 |
| Overnight Percent Controller Updates [%] | 100.00 ± 0.00 | 41.87 ± 13.16 () | 32.22 ± 10.67 (ii) | 25.52 ± 8.59 () |
| Overnight Energy Consumed [mAh] | 5.27 ± 0.36 | 2.21 ± 0.70 () | 1.71 ± 0.55 () | 1.36 ± 0.44 (**) |

Figure 3:
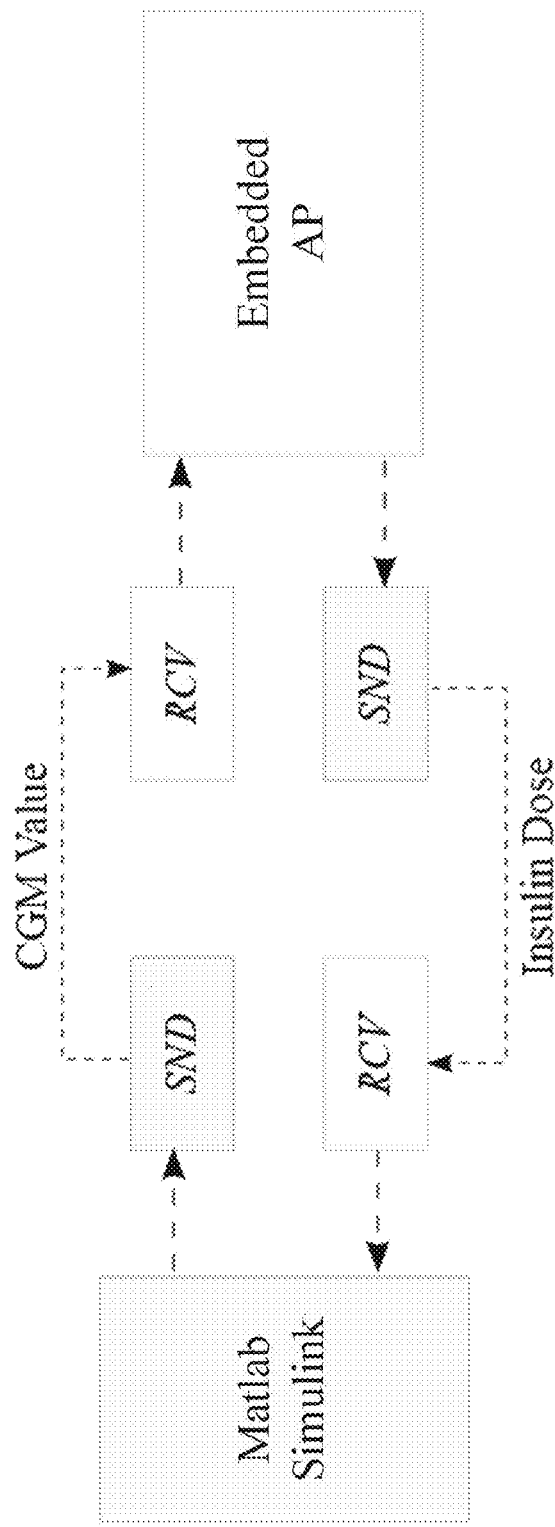
FIG. 3 is a schematic of testing the artificial pancreas in a hardware-in-the-loop setting.

FIG. 3 illustrates a hardware-in-the-loop implementation. SND and RCV denote sending and receiving data, respectively, via Bluetooth LE or WiFi.

C. Results and Discussion

The following results are obtained by testing the TT-ZMPC and ET-ZMPC on 111 in-silico subjects, obtained as follows: 100 subjects from the full version of the UVA/Padova simula-tor, 10 subjects from the short version of the UVA/Padova testbed, and 1 subject whose dynamics are generated by averaging the model parameters of the aforementioned 110 subjects.

1) Comparing TT-ZMPC and ET-ZMPC: We test the performance of the ET-ZMPC with $\varepsilon_{obs}$=1, 2, 3 mg/dL and compare with the standard TT-ZMPC for both announced and unannounced meals. For this comparative study, we report BG performance metrics (as recommended in [46]) in Table I for the overall study and overnight periods (12 AM to 8 AM; depicted with gray rows). To determine the efficacy of the proposed control strategy, we provide the percentage of controller updates required for each variant of the ET-ZMPC, along with power consumed in mAh over the simulation time. A DROK USB 2.0 digital multimeter is used to measure the current (in mA) flowing into the Raspberry Pi during the simulation time period. The average current value is then multiplied by the total time (in hour) required by the control module to solve the quadratic program (11) to yield an estimate of the total energy consumed. An implicit assumption is made in this estimation of the energy consumption: that the Raspberry Pi can be switched on/off instantaneously upon concluding communications with Simulink, and the idle current is negligible. Although this is not strictly true for the Raspberry Pi, embedded AP technology may employ application-specific hardware, the operation of which can be tightly tailored to the task of being energy-efficient, thereby minimizing idle current loss.

Figure 4:
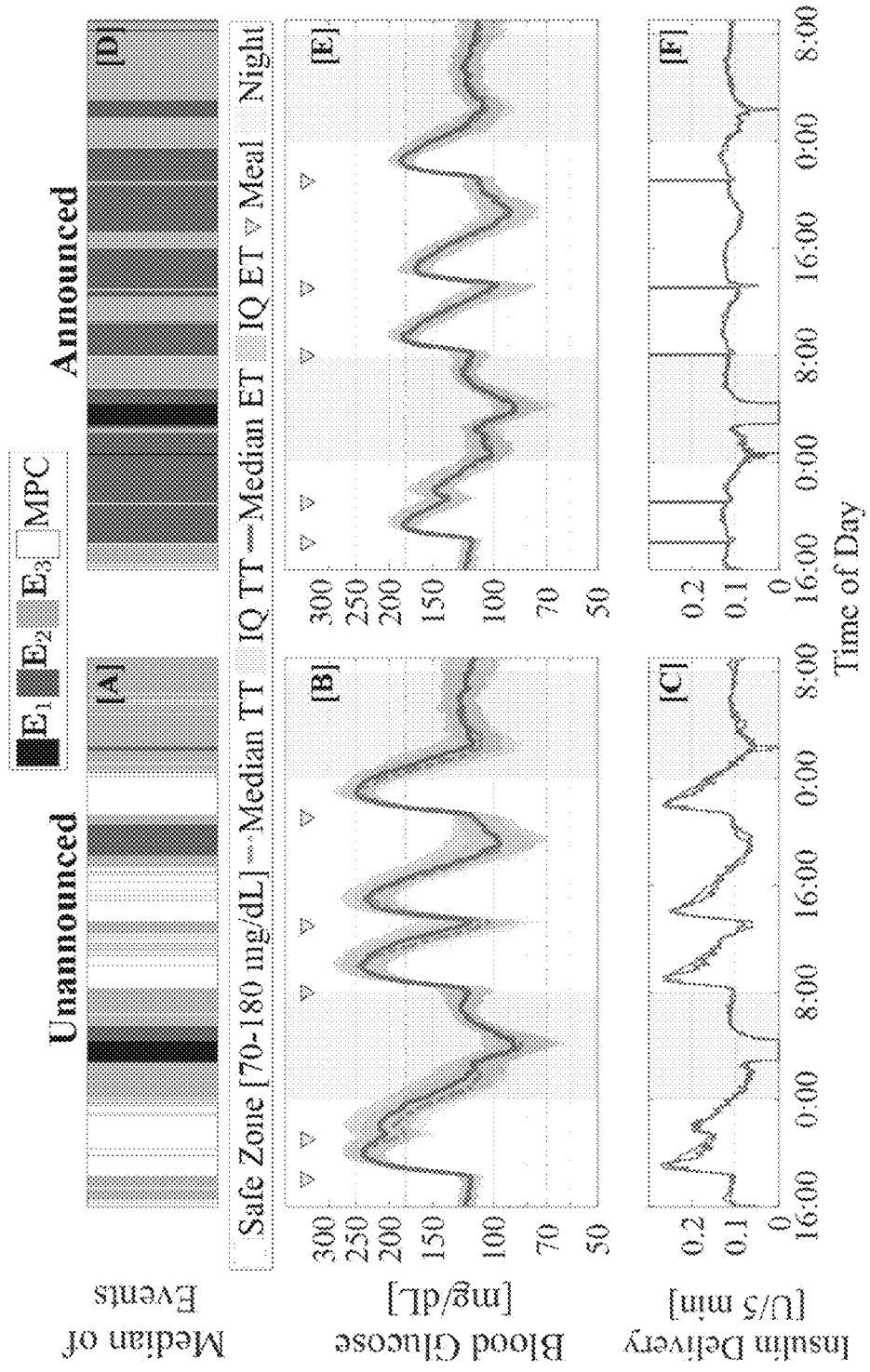
FIG. 4 are examples of graphs comparing the performance of the proposed algorithm to the classical controller in two settings: with and without meal announcement.

FIG. 4 illustrates the robustness analysis of the controller with mismatched basal insulin rate, carbohydrate ratio and total daily insulin intake. (Left column) Controller performance with unannounced meals. [A] Median of events over the closed-loop simulation. [B] Median and interquartile (IQ) ranges of blood glucose concentration for ET-ZMPC (blue) and TT-ZMPC (red). [C] Median insulin profiles for ET-ZMPC (blue) and TT-ZMPC (red). (Right column) Controller performance with meal announcements. [D] Median of events over the closed-loop simulation. [E] Median and interquartile ranges of blood glucose concentration for ET-ZMPC (blue) and TT-ZMPC (red). [F] Median insulin profiles for ET-ZMPC (blue) and TT-ZMPC (red). The spikes (truncated at 0.3U) denote the manual insulin boluses.

For unannounced meals, we note from Table I[A] that increasing $\varepsilon_{obs}$ results in a decrease of time spent with BG less than 70 mg/dL both overall and overnight. This is primarily due to anticipatory and conservative pump suspension: as expected, this results in (statistically significant) increased time spent above 180 mg/dL. The time spent in the euglycemic range, along with the median BG concentration, decreases with increasing $\varepsilon_{obs}$. This can be explained by recalling the condition for event E3: as $\varepsilon_{obs}$ increases, previously optimal, but currently suboptimal, control actions are employed with higher discrepancy between the CGM value and the estimated BG level. This suboptimality of controller decisions, coupled with the discrepancy in BG estimates, results in less tighter regulation of BG. However, this slight compromise (≈10% decrease of time in euglycemic range) in regulatory performance comes at an excellent trade-off: a 40-60% reduction in controller updates with less than half the energy consumed for overnight simulations (in comparison with the standard time-triggered controller), without a significant alteration of time in with BG<70 mg/dL.

The energy-saving capabilities of the proposed ET-ZMPC are more pronounced with meal announcement. We deduce from Table I[B] that the time in the BG ranges vary less than 2% for the ET-ZMPC versus the TT-ZMPC, while the controller updates are reduced by 67-80% and the energy consumed is less than half. At night, the ET-ZMPC maintains the subjects' BG in the euglycemic range more than 96% of the time in spite of the undetected 2 U insulin bolus with the controller in sleep mode for over 4 hours each night in spite of a sizable undetected insulin bolus (emulating a sudden, nocturnal hypoglycemic event).

A crucial question that remains unanswered is how to select a specific value of $\varepsilon_{obs}$ utilizing the above data collected for $\varepsilon_{obs}=\{1, 2, 3\}$. This is the topic of the next subsection.

Figure 5:
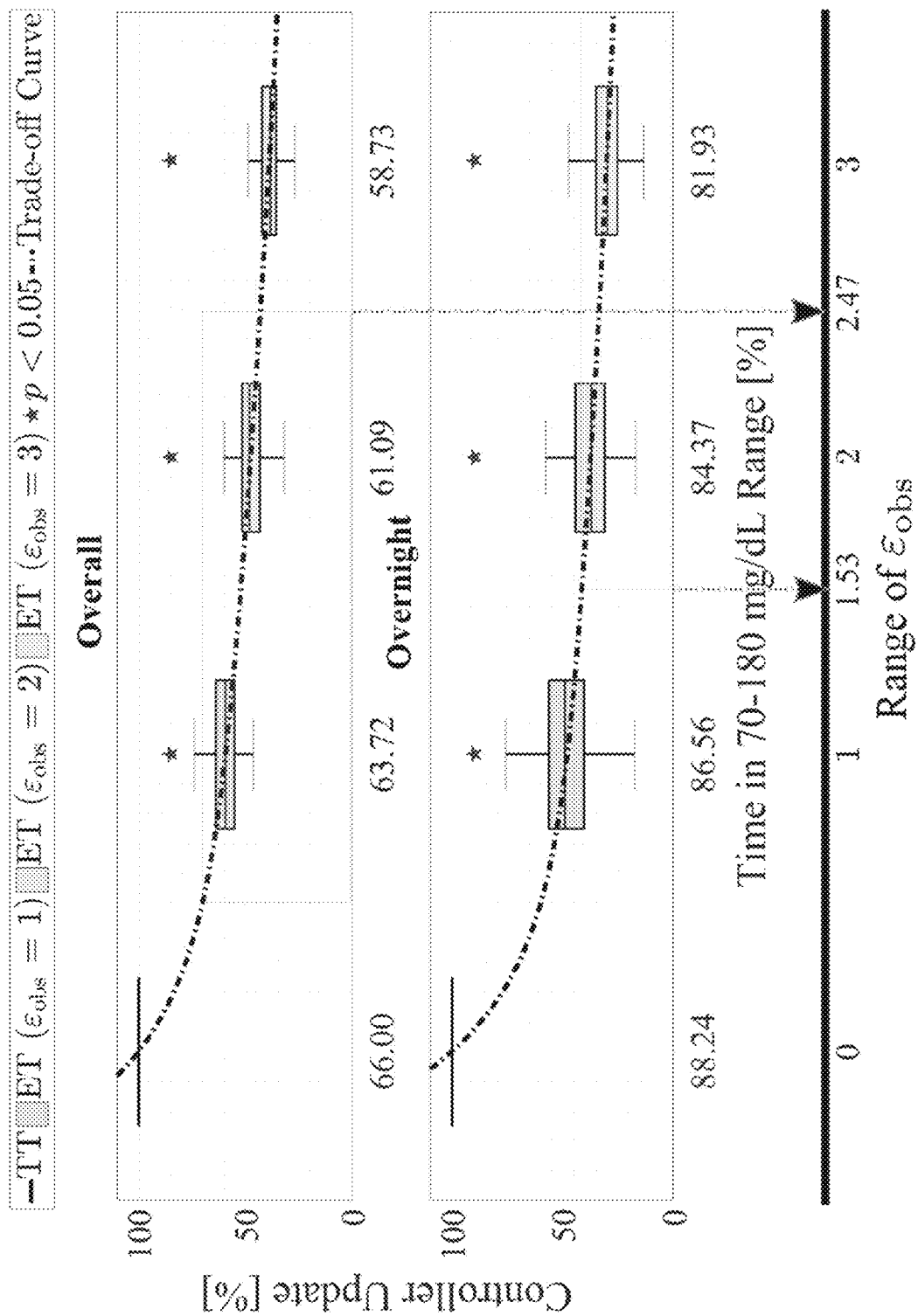
FIG. 5 is an example of a graph showing the trade-off between efficiency (percentage of controller updates) versus performance for a range of values of a tuning parameter $\varepsilon_{obs}$.

2) Selection of $\varepsilon_{obs}$ We propose the following systematic method of exploiting trade-off curves to select a particular value of $\varepsilon_{obs}$. Note that a fully automated AP should be capable of handling the case when meals are unannounced. Thus, from a safety perspective, it is important to leverage the controller performance data for unannounced meals to select $\varepsilon_{obs}$. We begin, therefore, by choosing trade-off metrics based on Table I[A]. Specifically, we select time in the 70-180 mg/dL range as the metric for glucose regulation performance, and the average controller update frequency for each $\varepsilon_{obs}$ as the efficacy performance. Of course, the designer could choose other metrics (e.g. time in 80-140 mg/dL) of performance as prioritized by their specific investigation. Next, we construct the trade-off curves by polynomial regression for the chosen metrics; this is illustrated in FIG. 5. The Pareto-optimal nature of the metrics are evident from the trade-off curve (black dash-dot line). The next step involves formulating an admissible design space: for example, we specify that for overall performance, we require at least a 40% reduction in controller update frequency, and at least 60% time in the euglycemic range. Additionally, we require that, overnight, we require at least 60% of sleep time for the controller, and maintenance at least 80% of the time in the euglycemic region in spite of the onset of latent nocturnal hypoglycemia. Leveraging our regression-based trade-off curve and these controller specifications, we construct the admissible design space shown by shaded yellow boxes in FIG. 5. Noting that the TT-ZMPC is equivalent to an ET-ZMPC with $\varepsilon_{obs}=0$ having predictive pump suspension, we assume a linear variation of $\varepsilon_{obs}$ from 0 to 3 along the trade-off curve, as depicted by the thick black line at the bottom of FIG. 5. Then the intersection of the admissible design spaces are projected onto the range of $\varepsilon_{obs}$ line (shown using red dashed arrows) to obtain an admissible range of $\varepsilon_{obs}$ in [1.53, 2.47].

For low-complexity/embedded implementations, the value $\varepsilon_{obs}=2$ is chosen as it offers a specific engineering advantage. Namely, it is represented using two-bits and therefore can be compared easily rather than using single precision and complicated multiplexers or combination of multiplexers. Comparing against $\varepsilon_{obs}=2$ can be done more efficiently by shifting $\|\Delta\gamma_k\|$ bitwise to the right (division by 2) and comparing with a single bit: that is, checking whether $\|\Delta\gamma_k\|2 \leq 1$ instead of $\|\Delta\gamma_k\| \leq 2$. This indicates that simple hardware components can be used to implement a swift comparison if $\varepsilon_{obs}=2$, as chosen for this exemplar design.

3) Resilience against model mismatch/misinformation: To verify the controller performance and controller update reduction with $\varepsilon_{obs}=2$ mg/dL in a challenging simulated setting, we test the TT-ZMPC and ET-ZMPC with the following (sizable) model mismatch: (i) a random perturbation of ±20% on the TDI value, (ii) ±50% additive uncertainty on the basal insulin infusion rate, and (iii) for announced meals, incorrect estimation up to ±25% of the carbohydrate ratio. The objective of introducing these uncertainties is to estimate the controller performance in spite of temporal variations in these parameters, and to take into account inaccuracy in model fitting. The user also misinforms the controller by ±25% of the estimated carbohydrate content in the meal: this is a very common occurrence, although we selected a high misinformation magnitude of 25% to challenge the controller and ensure operational safety in clinically adverse scenarios.

The results of this robustness analysis are presented in FIG. 4 for unannounced meals (subplots [A]—[C]), and meal announcement (subplots [D]—[F]). FIGS. 4[A] and [D] depicts the median of the event that was triggered at each time step. Both subplots show similar trends. The pump suspension E1 (black shade) closely follows the nocturnal injection of 2U of undetected insulin when the subjects enter the hypoglycemic range or when (in case of the announced meals) the meal size is incorrectly estimated leading to overbolusing of insulin. As expected, the event E2 (dark green shade) triggers postprandially, when the infused insulin drives the IOB upper bound to zero; this is more pronounced in the case of meal announcements since a large impulsive bolus is applied, so the duration for which $u_{max}^{IOB}=0$ is longer. Since the subplots [A] and [D] depict the median of the events, the white regions (illustrating controller updates) is mostly limited in case of announced meals, since the critical decision making during a meal is handled via manual bolusing, and thus, the MPC does not need to be invoked often. This is in contrast to the plentiful presence of controller updates in the case of unannounced meals, since the controller is solely responsible for decision making at the onset of a meal. We also draw attention to the fact that in the second night, when there is no latent hypoglycemia, and the IOB constraint is non-zero, the subplots [A] and [D] show that E3 is triggered. This can be explained from subplots [B] and [E], respectively. We observe that the BG levels are in the euglycemic zone without sharp variations between the estimated BG and CGM values; even with model mismatch, the controller does not require updating for more than half of the night. Subplots [B]-[F] testify that in spite of non-trivial mismatch and misinformation, the event-triggering strategies are robust and perform safely without frequent controller updates, and the time in the euglycemic range are quite similar.

We provide a detailed illustration of controller update frequency in the presence of mismatch/misinformation in FIG. 5. We verify that our design specifications during the selection of $\varepsilon_{obs}=2$ are satisfied: indeed, the controller is idle 55% of the time (median) overall, and around 65% of the time at night when meals are unannounced: the time no controller updates are required improves to 71% and 77%, respectively, when meals are announced. Furthermore, the time in the euglycemic range is 62% overall, and 80% overnight for unannounced meals. For announced meals, these numbers are 86% and 92%, respectively.

D. Testing on Clinical Data

Figure 8:
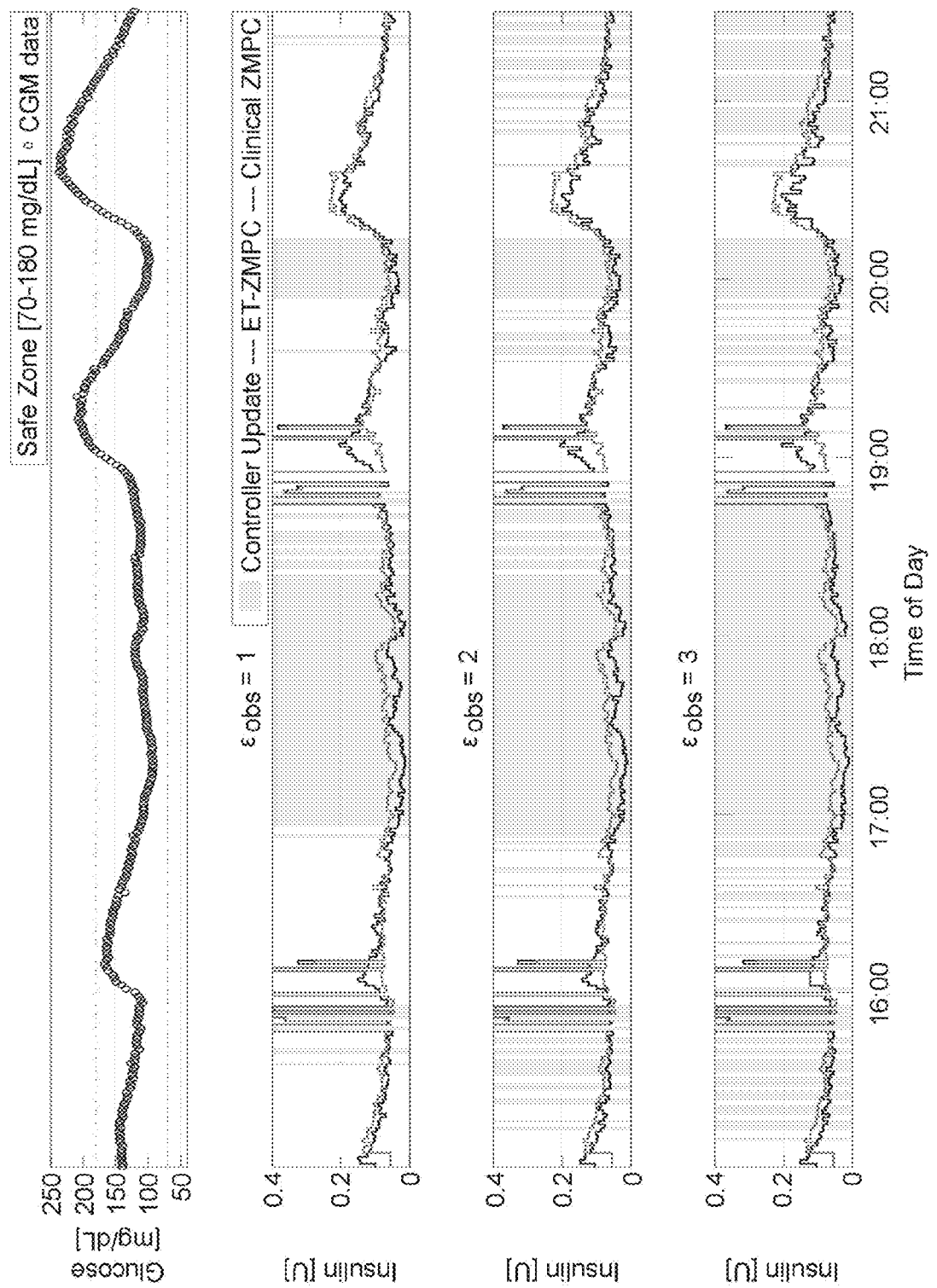
FIG. 8 shows example graphs illustrating clinical evaluation of ET-ZMPC using advisory mode with varying $\varepsilon_{obs}$ (a tuning parameter) on clinical data.

To estimate the performance of our proposed algorithm with sensor noise and glucose variability, we test the algorithm with $\varepsilon_{obs}=1, 2, 3$ mg/dL on clinical data t obtained in a randomized, crossover trial with 17 people with T1D in closed loop with MPC [13]. We evaluate our proposed algorithm on the CGM trace and compute the percentage time the processor implementing the ET-ZMPC can remain idle. We use the same MPC parameters as in the previous section, which differs from those used in the clinical study. In FIG. 8, the median insulin traces over 17 patients are compared with the actual MPC control obtained in the clinical study. Based on clinical data from a closed loop study that used the Dexcom G4 with the 505 algorithm (Dexcom, San Diego, CA), the percentage savings in controller updates for our proposed controller is statistically significant in all three cases (p<0.001) based on a Wilcoxon rank sum test, and the percent updates required decrease consistently with increase $\varepsilon_{obs}$. Specifically, the median percent updates required are 48.60, 40.36 and 34.64 for the ET-ZMPC tested on this data for $\varepsilon_{obs}$=1, 2, 3 mg/dL, respectively. This can be deduced from the increasing density of the blue shades in FIG. 8. Albeit with limited updates, the control actions of the ET-ZMPC and the clinical ZMPC exhibit statistically similar trends, with total insulin infused being slightly lower: specifically, clinical: 39.64±12.14 U, $\varepsilon_{obs}$=1 mg/dL: 36.79±8.83 U (p=0.58), $\varepsilon_{obs}$=2 mg/dL: 35.97±8.65 U (p=0.39), $\varepsilon_{obs}$=3 mg/dL: 35.33±8.56 U (p=0.27).

FIG. 5. Illustrates box-and-whisker plots to compare the TT-ZMPC and ET-ZMPC strategies in terms of trade-off between glucose regulation (median time in the 70-180 mg/dL range) and percentage of controller updates required in closed-loop over the entire simulation and during the night-time with and without meal announcement. Statistical significance is shown with blue stars and regression-based trade-off curves are depicted using gray dashed lines. Note that the x-axis is reversed.

Figure 6:
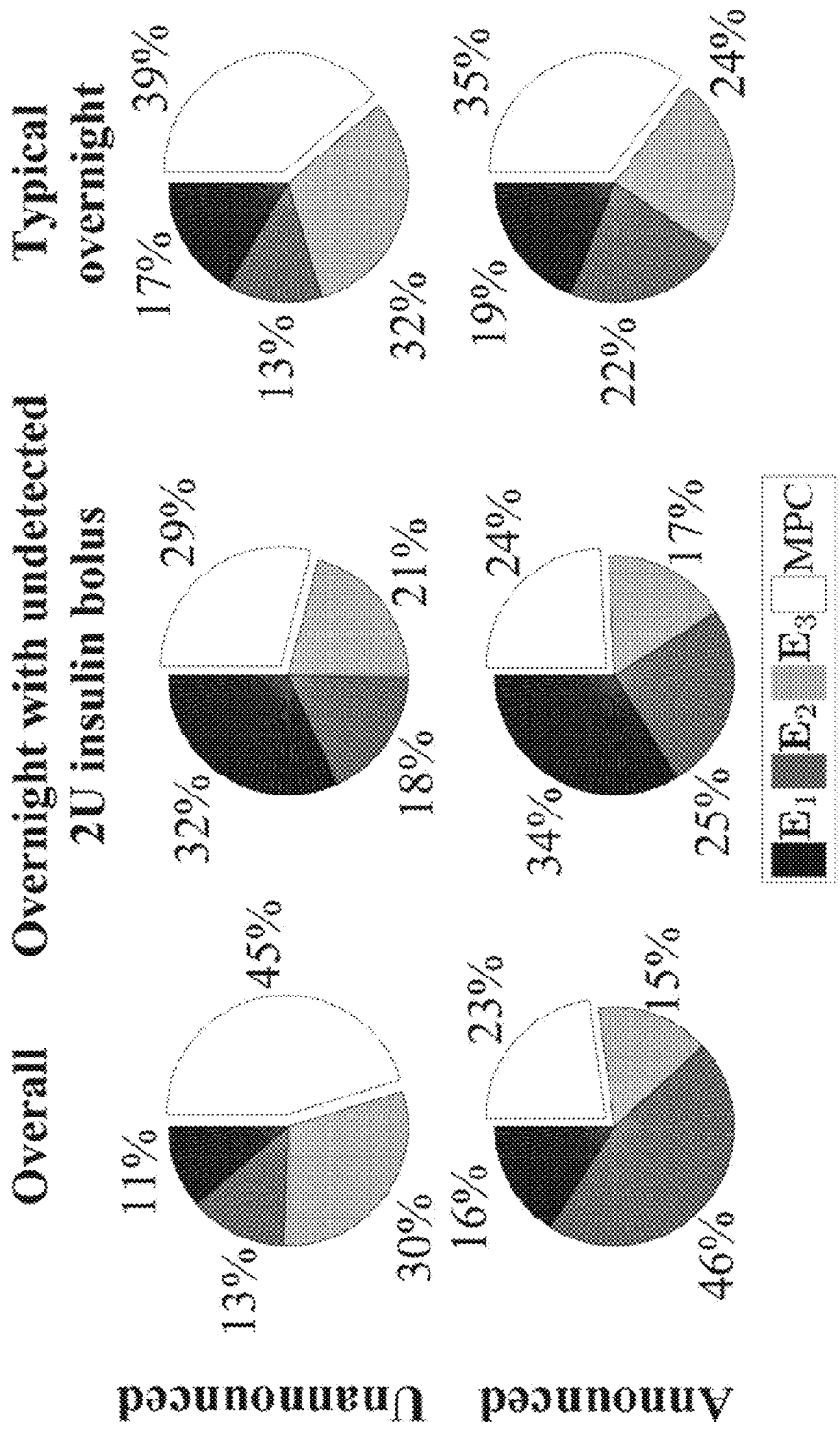
FIG. 6 are example pie charts showing the distribution of events reported for the overall simulation time for announced and unannounced meals.

FIG. 6 illustrates pie charts of the distribution of events of the ET-ZMPC ($\varepsilon_{obs}$=2 mg/dL) reported for the overall simulation time, the night-time with an undetected 2U insulin bolus, and a night-time without meals or latent hypoglycemia. (Top) Scenario of unannounced meal disturbances. (Bottom) Scenario of announced meal disturbances.

Figure 7:
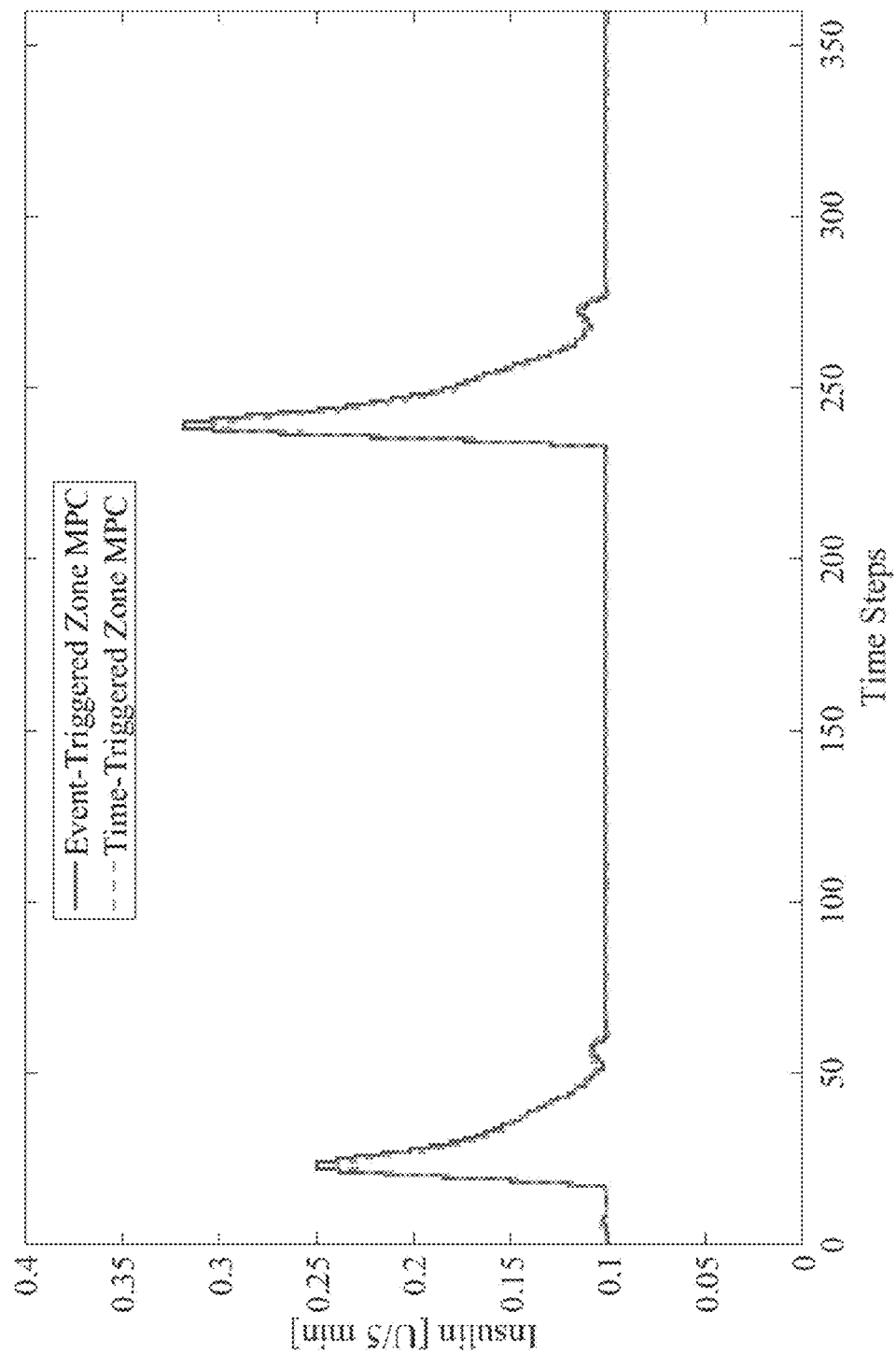
FIG. 7 is an example graph of a probability density function of variability in blood glucose for 17 subjects obtained from clinical CGM data.

FIG. 7 illustrates a graph showing the glucose variability histogram of clinical CGM data obtained from [13].

Although the total insulin used is lower the mean insulin delivered (shown in FIG. 8) exhibits a dispersion of announced meal boluses around 16:00 and 19:00, and a slight rise of insulin following a meal. These phenomena can be explained as follows. In the clinical study, announced meals were provided shortly before/after 16:00 and 19:00 but not exactly at those times: this is why we see a dispersion in the announced bolus timings. The slight rise (on average) of the ET-ZMPC control action versus the clinical ZMPC is due to event E2. This event is triggered due to higher levels of glucose due to the meal, in conjunction with a sharp decay of $u_{max,k}^{IOB}$ to zero following a meal bolus. This infusion of basal following the meal bolus raises the average insulin in the ET-ZMPC above the clinical controller (which computes infusions lower than basal).

FIG. 8 illustrates a clinical evaluation of ET-ZMPC using advisory mode with varying $\varepsilon_{obs}$ on clinical data. The lower three plots compare mean insulin profiles of the ET-ZMPC (black) and the clinical controller (red) for 17 patients, where the background blue shading denotes times when the control module processor can be switched off.

Example 7: Simulation of Event-Triggered SetPoint MPC

Figure 11:
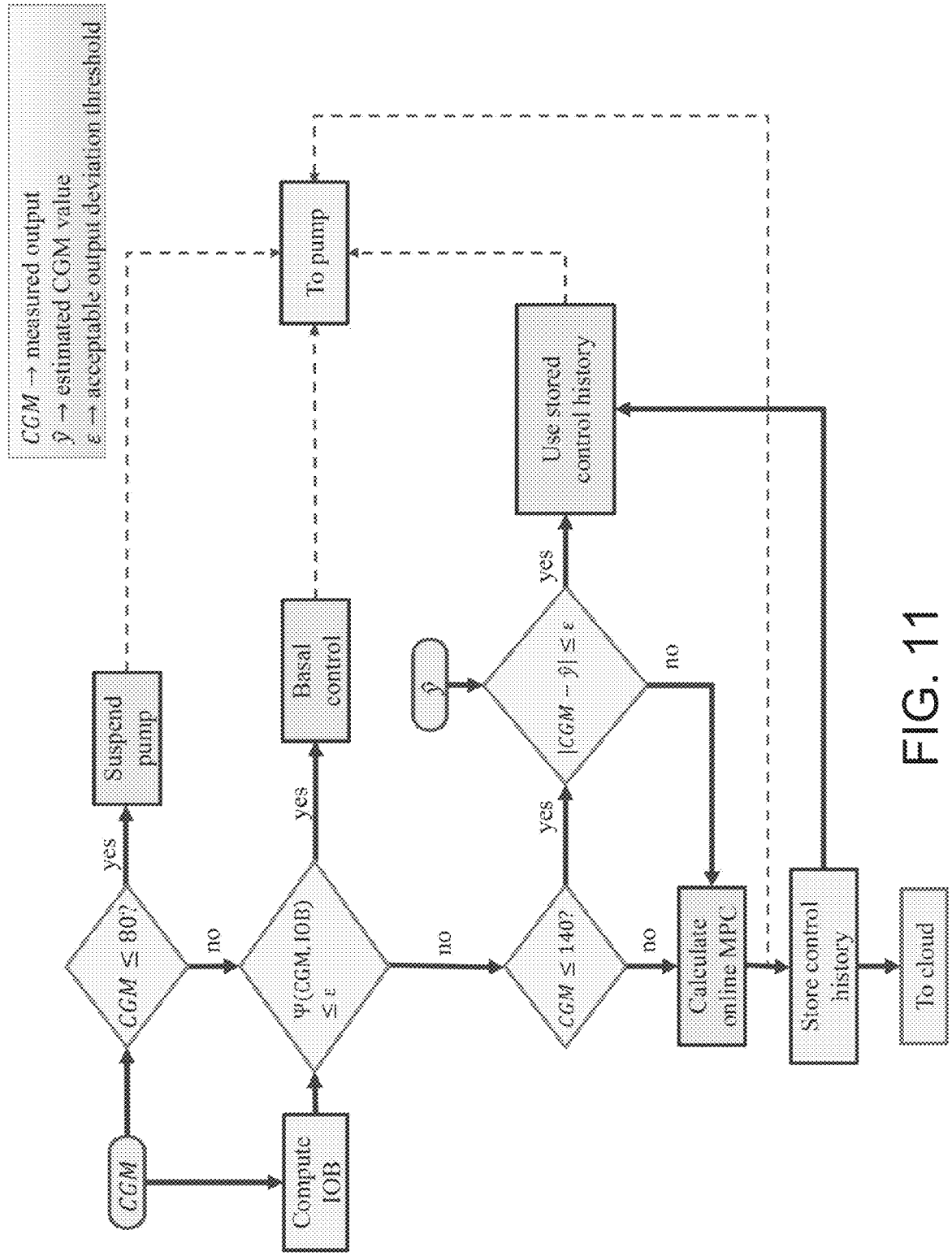
FIG. 11 is an example of a flowchart detailing the triggering factor for events used in event-based updating of a control algorithm for delivering insulin in an artificial pancreas.

In another example, the inventor(s) developed a proposed algorithm to be simulated using a hardware-in-loop ("HIL") simulation. FIG. 11 illustrates a schematic overview of the proposed algorithm for the event-triggering formulation. As illustrated, the control history has to be stored securely to save computation time in future instances; such storage could be in a secure server, in a mobile device 160, or on the CGM 140 or other suitable locations.

The current CGM value can be leveraged to compute system states using a state estimator. Based on the estimate of the state, we can compute an estimate of future outputs "y". Then the output deviation can be defined as the absolute value of CGM−Y. If this quantity is small, this indicates that the output of the model is relatively close to the CGM value.

If the current CGM output drops below a prescribed value (considered to be mg/dl), we suspend the pump immediately; this is a common strategy in AP formalisms for reducing hypoglycemic events. We choose our second triggering variable to be the IOB constraint. The IOB constraint is defined as:

$$\Psi(CGM, IOB) = \frac{CGM - G_{ref}}{CF} - IOB,$$

Accordingly, CGM is the current glucose measurement, $G_{ref}$ is the desired glucose concentration, CF is the patient-dependent correction factor, and IOB is the current insulin on board. When the IOB constraint indicates that the insulin level in the patient system is too high to warrant additional large doses of insulin, we switch the controller off, and the pump supplies basal insulin. Third, if the current CGM value is within a prescribed zone (herein selected to be a commonly used zone: 80-140 mg/dl) and the output deviation discussed in the previous paragraph is less than a pre-determined value e (chosen to be 1.0 in this work), then the previously computed control action is applied. In general, event-triggered MPC formulations with control horizon $N_u$, all $N_u$ steps of the control trajectory of the MPC are implemented if the output deviation is small. If none of the above conditions are triggered, then the usual quadratic programming problem (QP) is solved, and an MPC control value is computed. This insulin dose is then applied, and the control actions are stored securely (perhaps on a server storage platform) for possible future use.

The inventors implemented the proposed event-triggered MPC based AP on a simulated patient system with unannounced 50 g and 70 g carbohydrate meals. In this section, we illustrate our proposed event-triggered setpoint MPC (a specific case of the zone MPC where the upper and lower bounds of the zone coincide to a single value) in a HIL framework. We demonstrate the performance of this proposed controller as a standalone algorithm for the AP in FIG. 12A and provide comparison plots (with time-triggered MPC) in FIG. 13A.

Figure 12A:
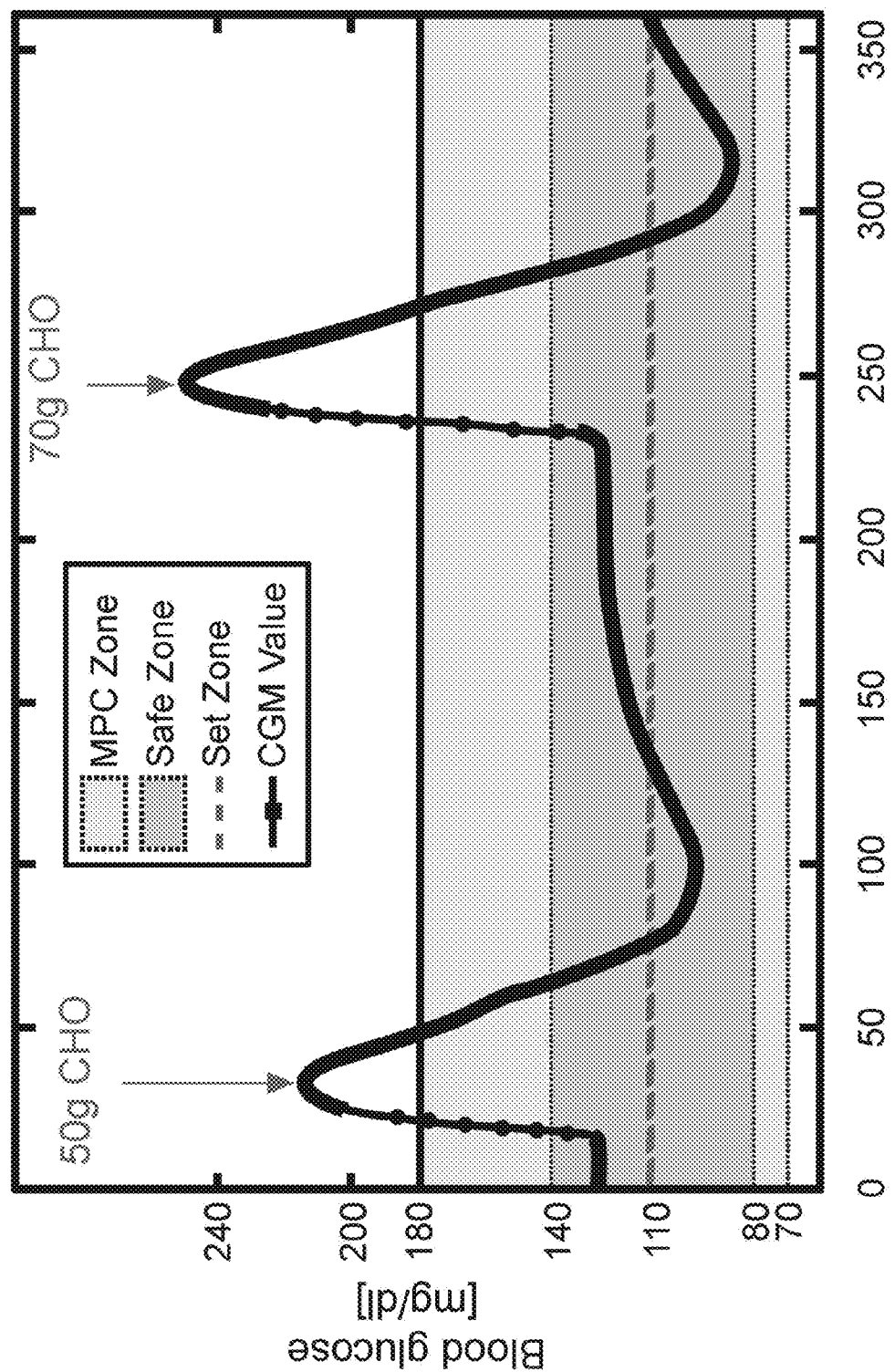
FIG. 12A is an example of a graph showing a glucose response with unannounced meals shown using arrows.
Figure 12B:
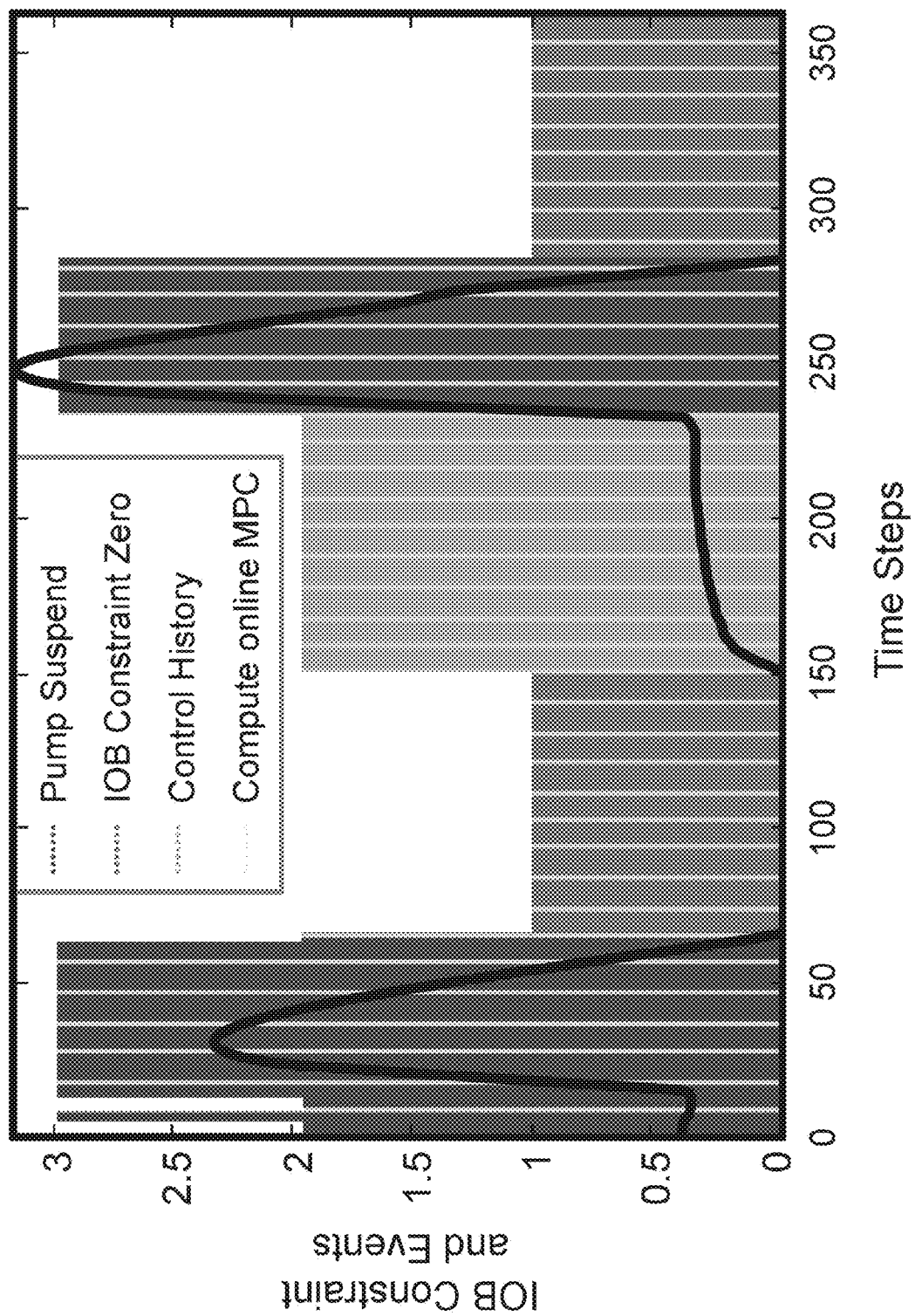
FIG. 12B is an example of a graph showing IOB constraint and event-selection using the proposed algorithm; trajectory.
Figure 12C:
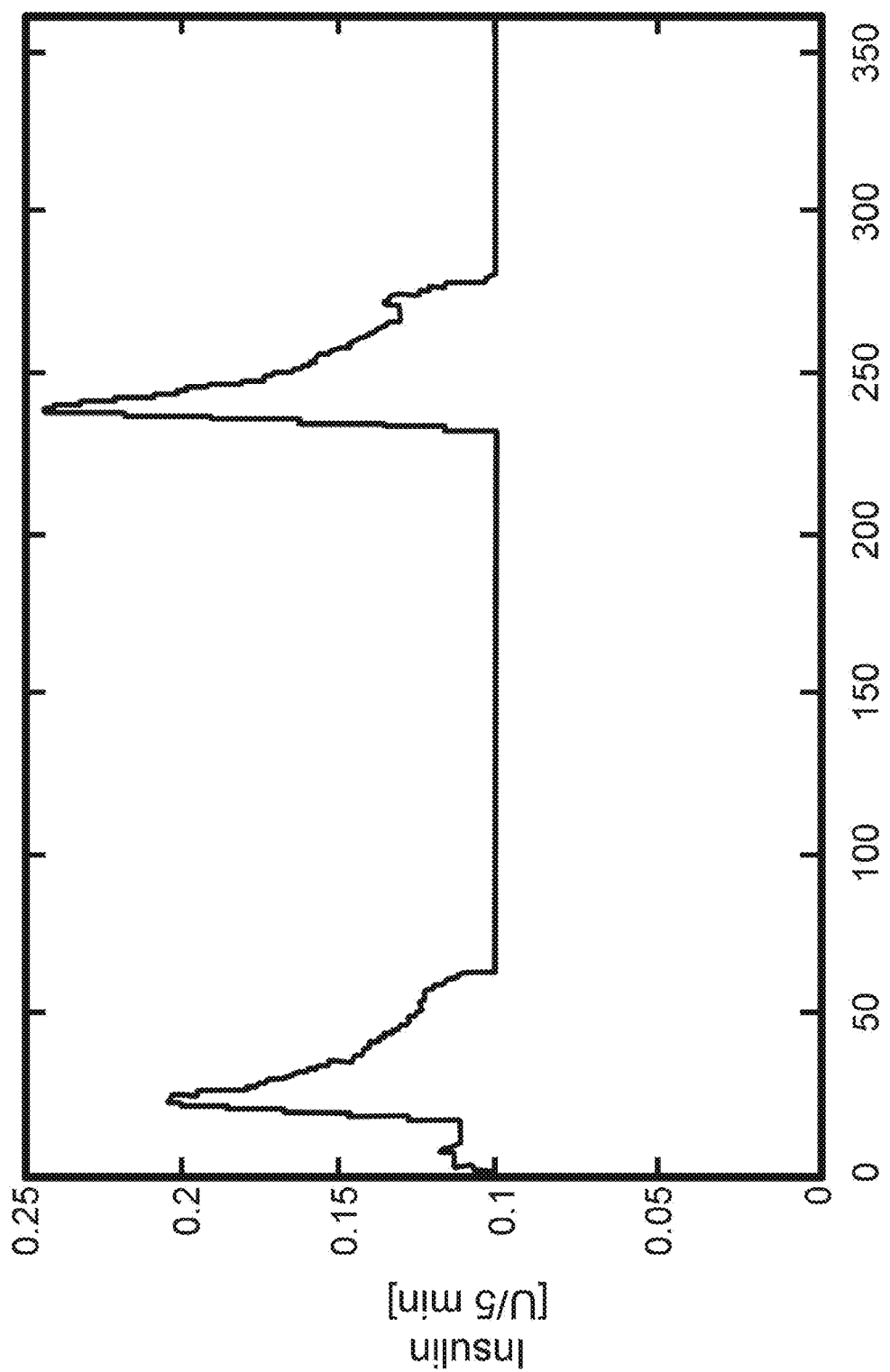
FIG. 12C is an example of a graph showing a computed insulin dose
Figure 12D:
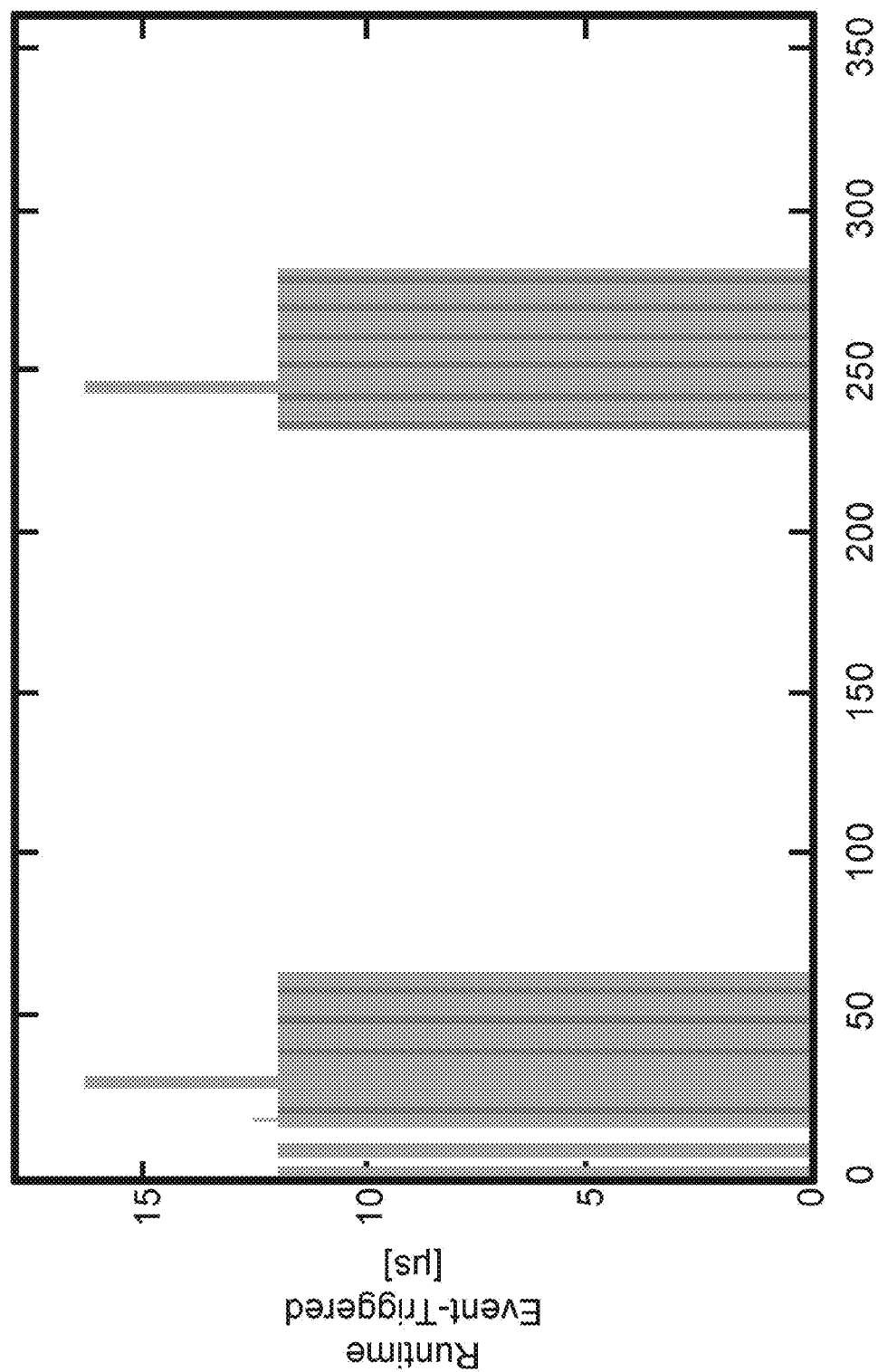
FIG. 12D is an example of a graph showing execution times in micro-seconds for an event-triggered MPC.

FIGS. 12A-12D illustrate performance of event-triggered Set Point-MPC based AP. FIG. 12A illustrates the glucose response with unannounced meals shown using red arrows. The set point is considered to be 110 mg/dl. The inner zone is 70-140 mg/dl and the outer clinically safe zone is 70-180 mg/dl. FIG. 12B illustrates IOB constraints curve and event-selection using the proposed algorithm. There is no pump suspension in this exemplar simulation, but solution of the QP is reduced considerably, with previous control values used where possible and basal insulin provided when the IOB constraint is zero. FIG. 12C illustrates the computed insulin dose trajectory. FIG. 12D illustrates execution times in micro-seconds for the event-triggered MPC.

Figure 13A:
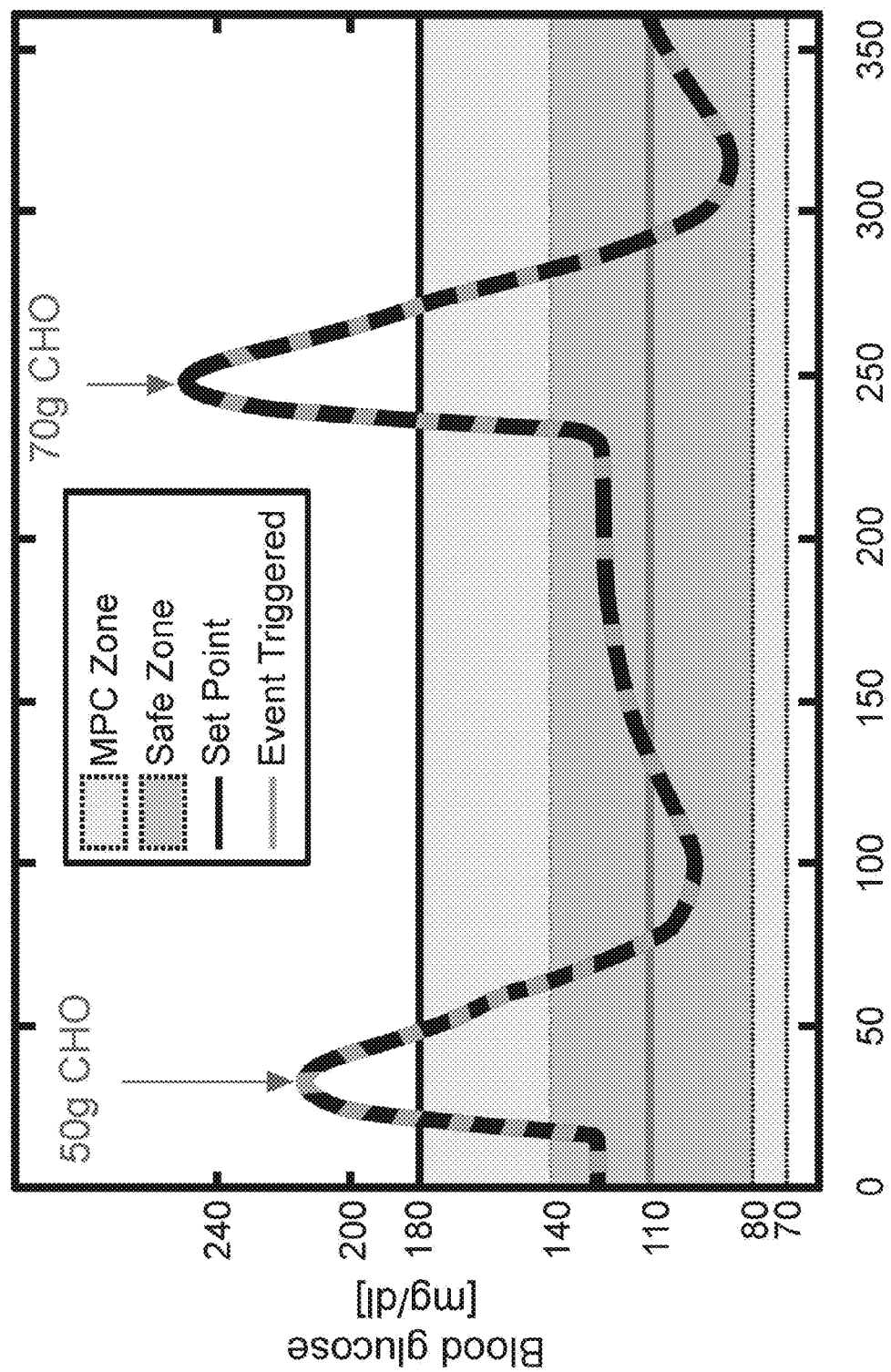
FIG. 13A is an example of a graph showing a comparison of glucose responses of event-triggered and time-triggered set-point MPC based AP.
Figure 13B:
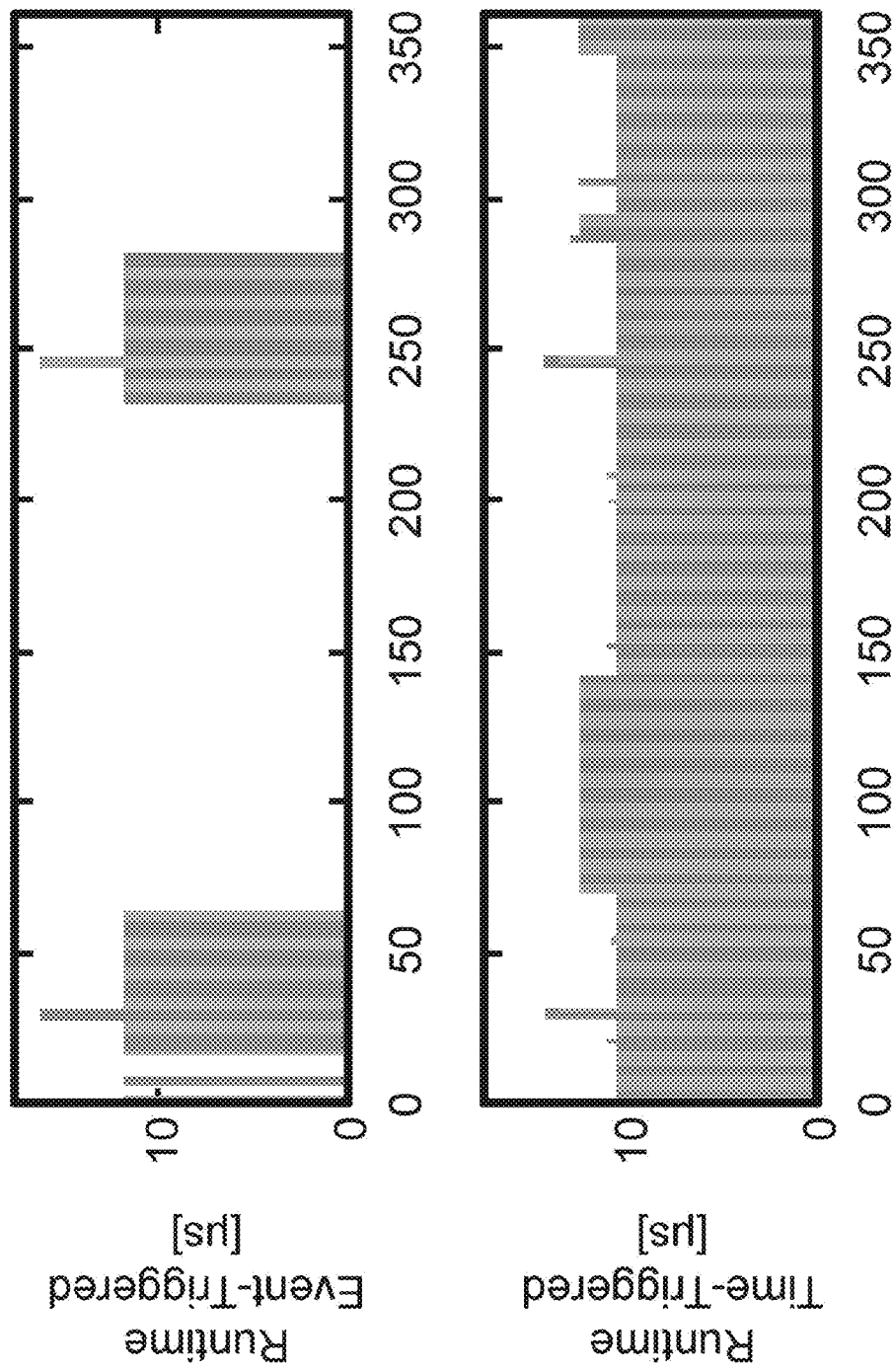
FIG. 13B is an example of a graph showing a comparison of execution times in micro-seconds for event-triggered and time-triggered set-point MPC.
Figure 13C:
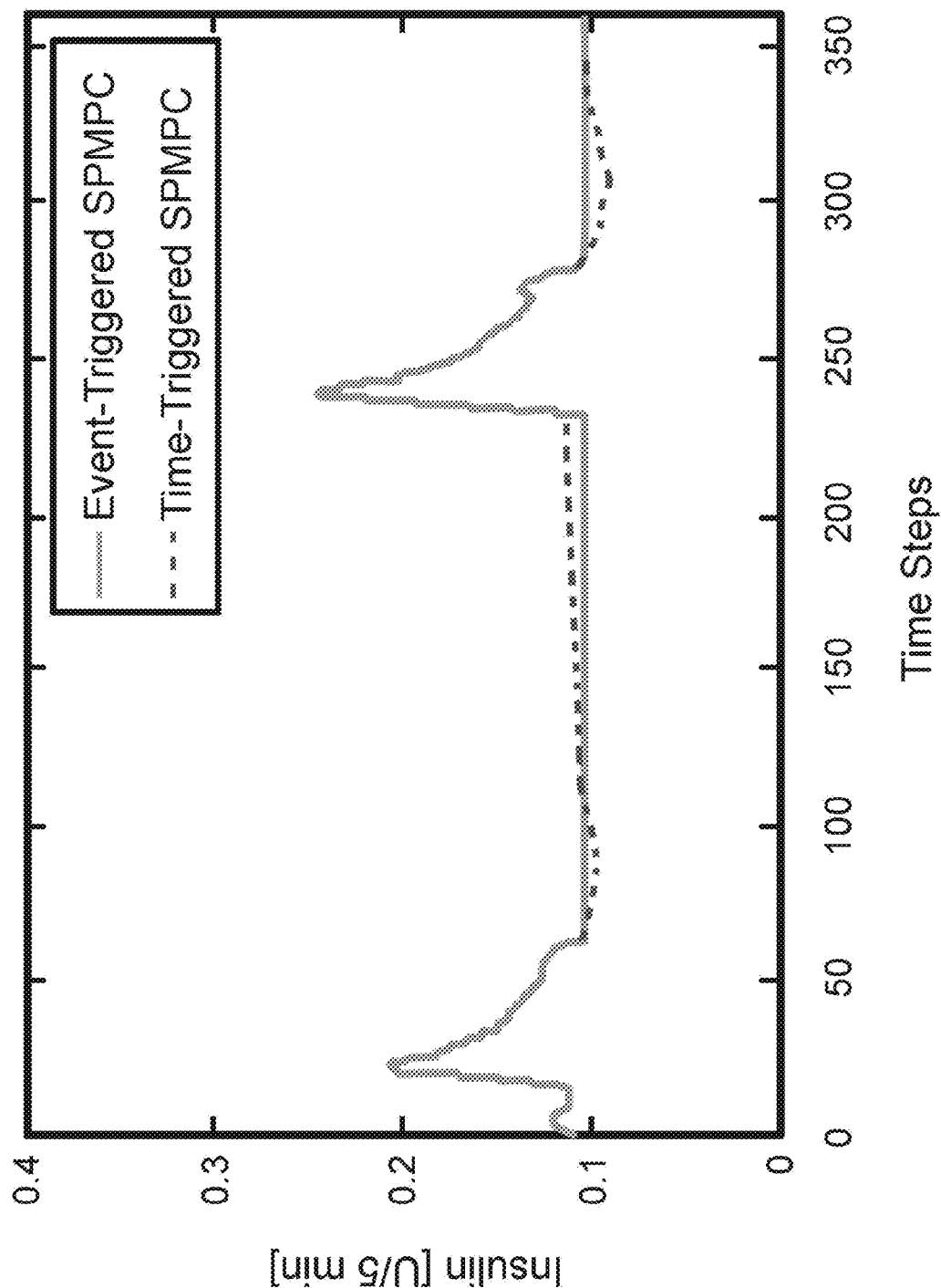
FIG. 13C is an example of a graph showing a comparison between computed insulin doses for event-triggered and time-triggered set-point MPC.
Figure 13D:
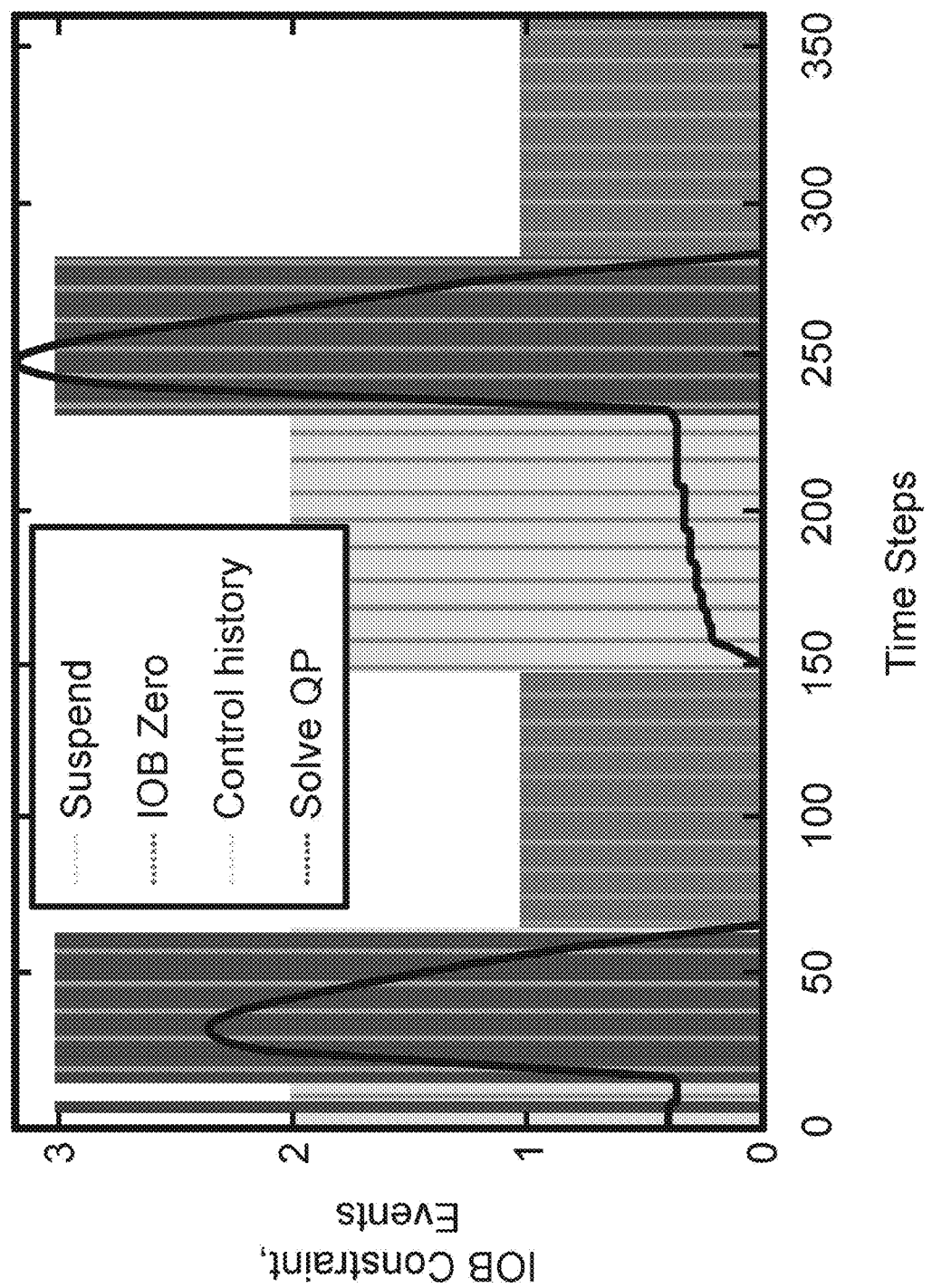
FIG. 13D is an example of a graph showing IOB constraint and event-selection using the proposed algorithm.

FIGS. 13A-13D illustrate the comparison of event-triggered and time-triggered Set Point-MPC based AP. FIG. 13A illustrates a comparison of glucose responses. FIG. 13B illustrates a comparison of execution times in micro-seconds for event-triggered MPC and time-triggered MPC. FIG. 13C illustrates computed insulin doses. FIG. 13D illustrates an IOB constraints curve and event-selection using the proposed algorithm. The solution of the QP is reduced considerably, with stored control values used where possible and basal insulin provided when the IOB constraint is zero.

In FIGS. 13A-13D, we observe that the controlled glucose trajectory of the time-triggered and event-triggered controllers is identical, and there is hardly any disparity between the control action sequences recommended by the controllers. However, as illustrated in FIG. 13B, the time-triggered approaches continuously run the QP solvers, while in the event-triggered approach, the controller can be safely switched off when event triggering conditions are satisfied, resulting in identical closed-loop glucose dynamics.

The performance of the event-trigged zone MPC is compared to the time-triggered zone MPC and presented in FIGS. 14A-14D. We can observe that the control action recommended by the two controllers is identical resulting in identical glucose responses. However, the event-triggered MPC can be safely switched off resulting in significant computational savings compared to time-triggered MPC that needs to run continuously.

Figure 14A:
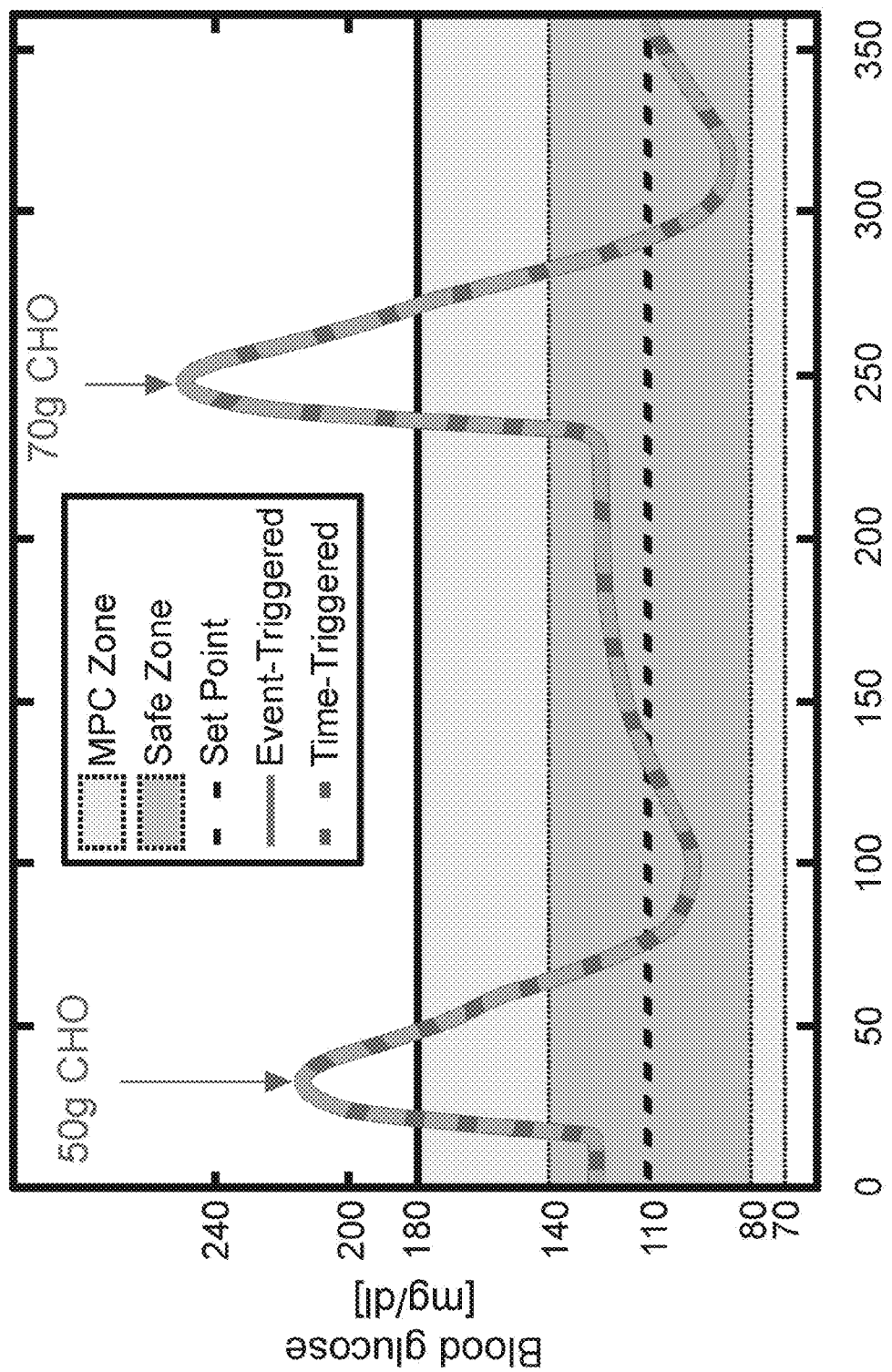
FIG. 14A is an example of a graph showing a comparison of glucose responses of event-triggered and time-triggered Zone-MPC based AP.
Figure 14B:
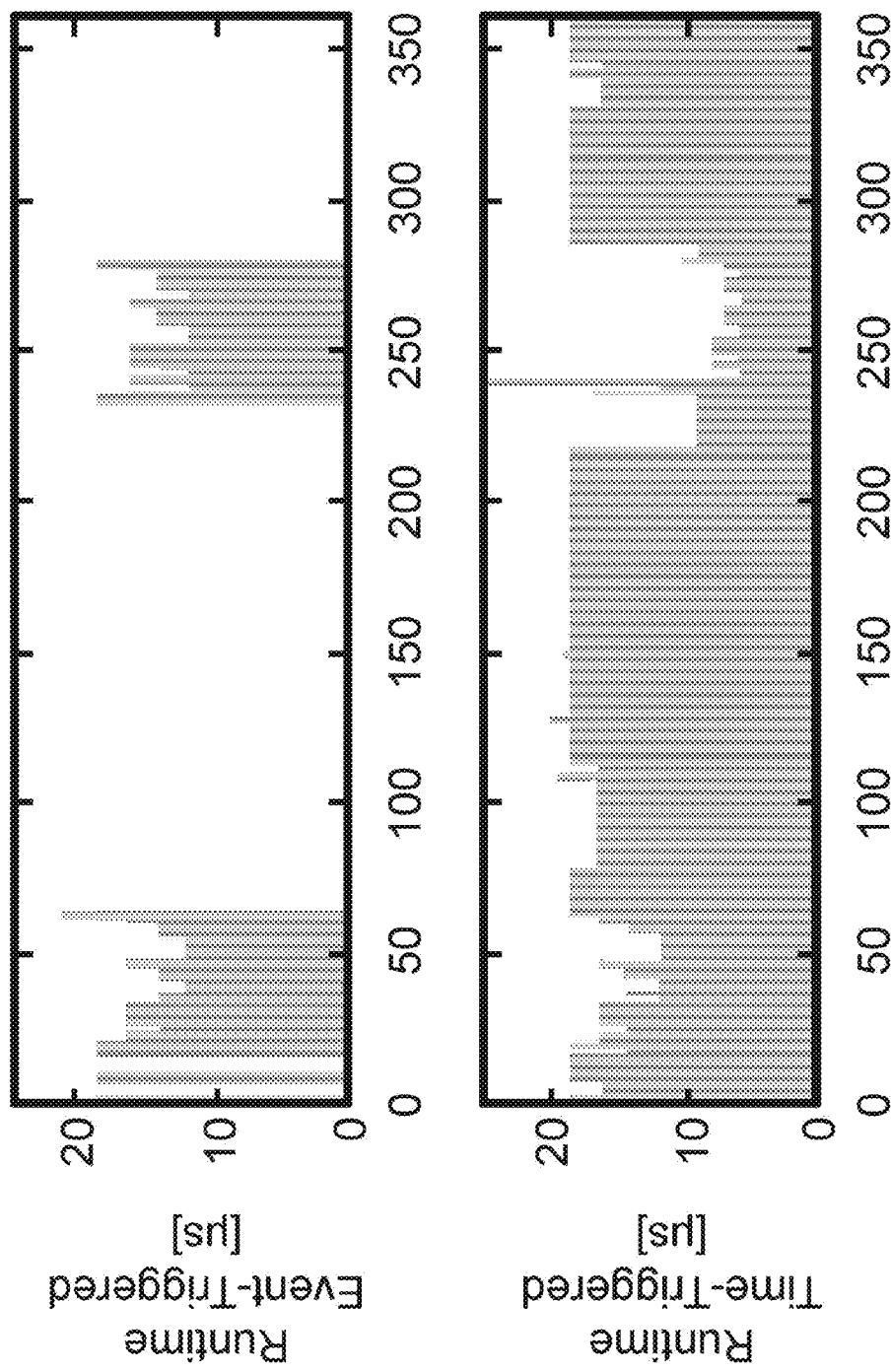
FIG. 14B is an example of a graph showing a comparison of execution times in micro-seconds for event-triggered and time-triggered Zone MPC.
Figure 14C:
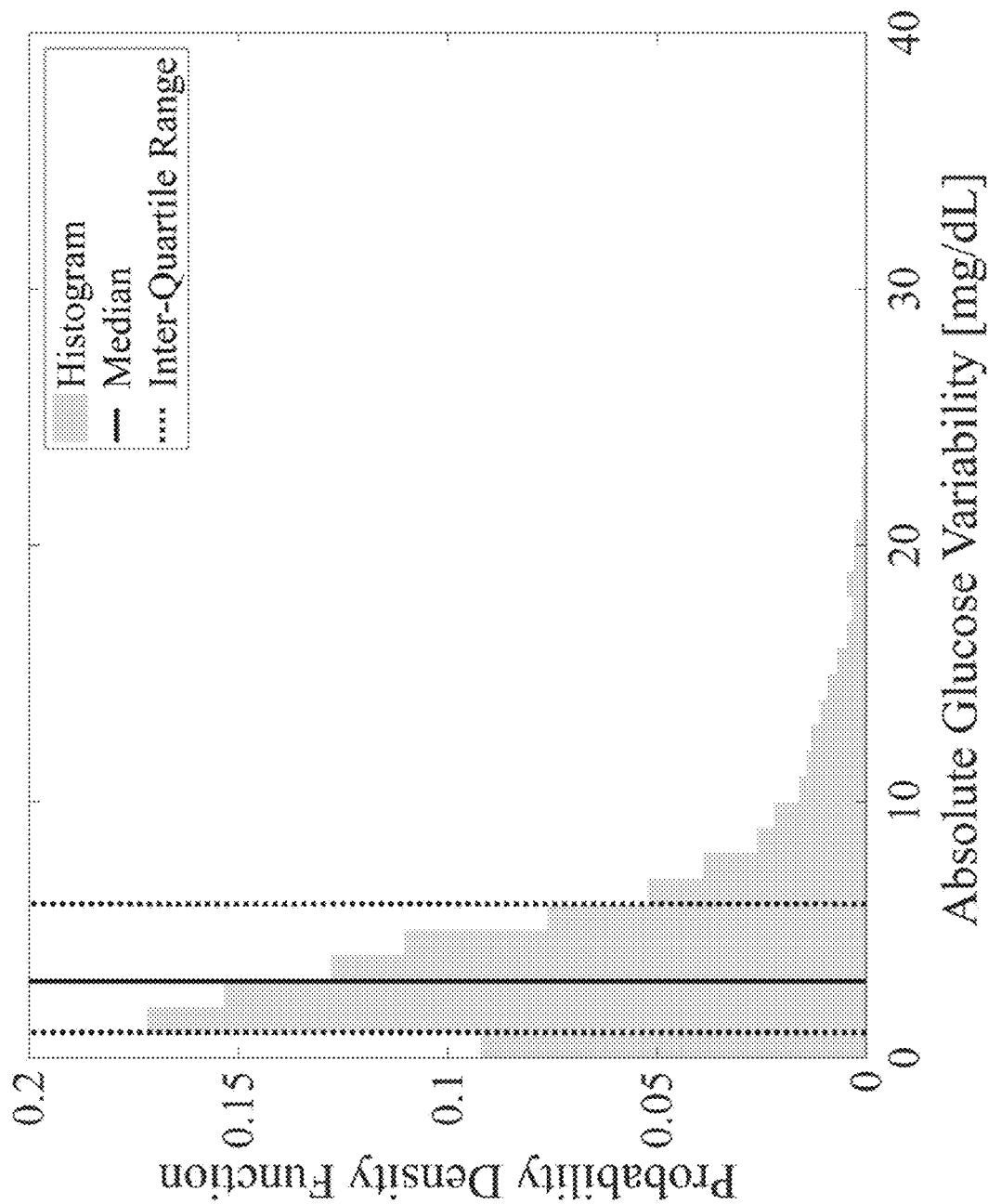
FIG. 14C is an example of a graph showing a comparison between computed insulin doses for event-triggered and time-triggered Zone MPC.
Figure 14D:
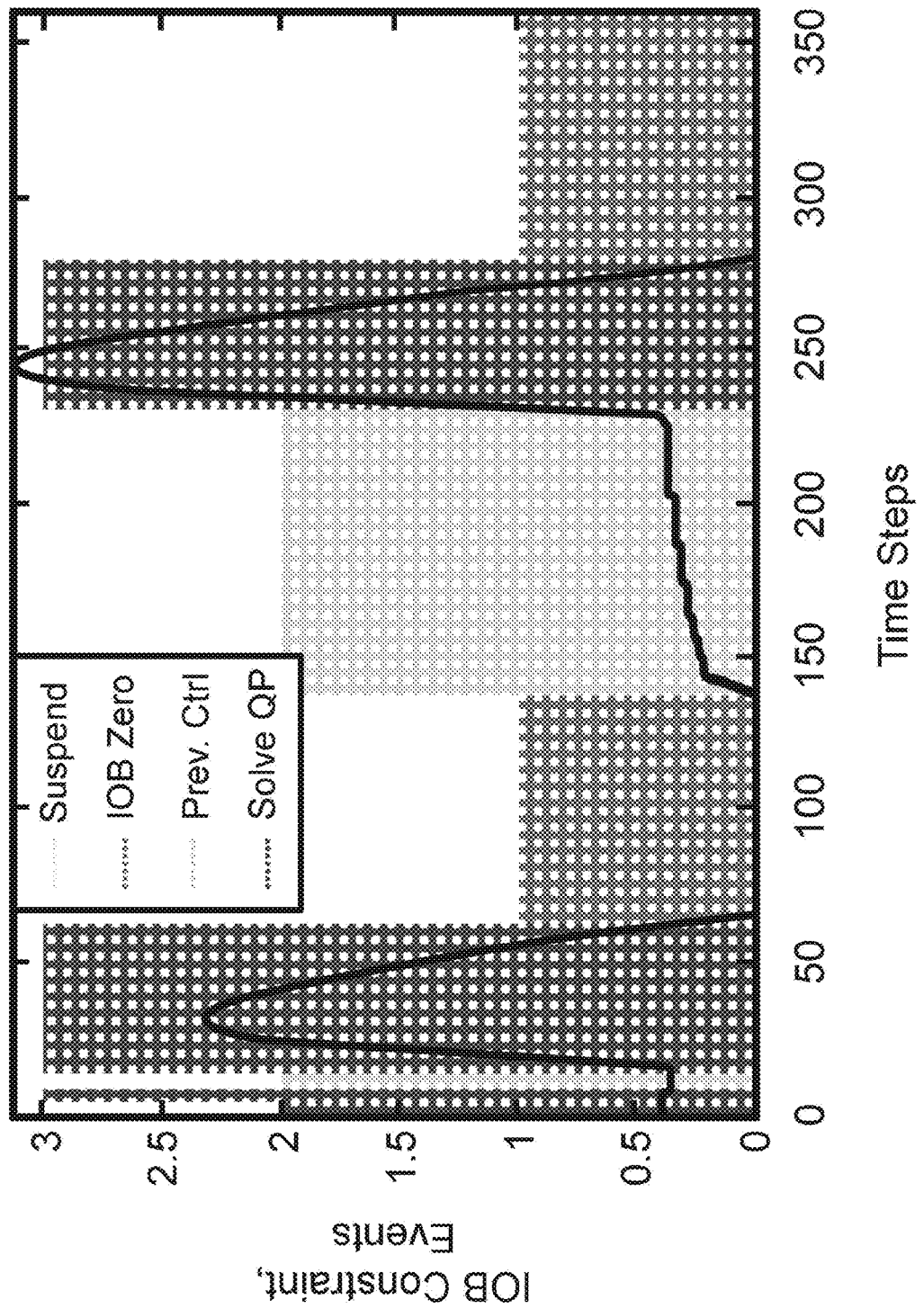
FIG. 14D is an example of a graph showing IOB constraint and event-selection using the proposed algorithm.

FIGS. 14A-14D illustrate the comparison of event-triggered and time-triggered Zone-MPC based AP. FIG. 14A illustrates the comparison of glucose responses. FIG. 14B illustrates the comparison of execution times in microseconds for event-triggered MPC and time-triggered MPC. FIG. 14C illustrates the computed insulin doses. FIG. 14D illustrates the IOB constraints curve and event-selection using the proposed algorithm. The solution of the QP is reduced considerably, with stored control values used where possible and basal insulin provided when the IOB constraint is zero.

A detailed study of the computational savings of the event-triggering strategies in comparison with the time-triggering strategies is presented in Table 2. Specifically, we note that in the time-triggering set point and zone MPC formalisms, the control module is powered on continuously, whereas the event-triggering results in the controller being powered off >70% of the simulation time. This implies that out of 42 simulated hours, we can switch off the controller for almost 30 hours. By extrapolating, we can expect that a battery that runs the time-triggering control module continuously for 1 day (24 hours) can run an event triggered AP for 80 hours (roughly 3 and one-third days), which is a sizeable improvement of battery life. Note that this is a rough estimate. To validate this estimate, we provide a further comparison of the total amount of time the control module is switched on to compute optimal MPC actions. For both the set-point and Zone MPC, the time-triggered version requires about 3 (almost 4 for Zone MPC) times the amount of time to compute MPC actions than the event-triggered version. This further supports our previous estimate of three times the longevity of battery life.

TABLE 2

Comparison of runtimes in event-triggering and time-triggered MPC

|  | Time-Triggered | Event-Triggered |
| --- | --- | --- |
| Set Point MPC | | |
| Percent Time Controller is ON | 100% | 29.36% |
| Total Simulation Execution Time (ms) | 4.5290 | 1.3197 |
| Zone MPC | | |
| Percent Time Controller is ON | 100% | 28.53% |
| Total Simulation Execution Time (ms) | 5.7626 | 1.5522 |

An open challenge that remains is the judicious use of communication strategies for the storage and retrieval of patient data. In the above event-triggered control formalism, it is observed that for large tracts of time (such as between 70 and 200 time steps), the control action is produced as a result of an event triggering not the solution of a QP. It is expected that CGM and AP control action data can be stored over this time interval on-chip rather than initiate communication to an external device for upload. Such a judicious use of on-chip memory and aperiodic uploading to a secure cloud platform will result in further energy savings on an embedded device. This idea is a small cog in the larger idea of 'event-triggered sensor design', where sending and retrieval of data from an external source (such as the cloud) can be performed upon the occurrence of an event, rather than periodically or continuously. Such events may include: manual triggering by the end-user in case he/she wishes to monitor their health status, sudden jumps in CGM measurements, or detection of meals/exercise, upon which alarms or rescue boluses may be prescribed by the health monitoring systems.

REFERENCES

[1] S. J. Russell, M. A. Hillard et al., "Day and night glycemic control with a bionic pancreas versus conventional insulin pump therapy in preadolescent children with Type 1 Diabetes: a randomised crossover trial." *Lancet Diabetes Endocrinol.*, vol. 4, no. 3, pp. 233-243, 2016.

[2] M. Tauschmann, J. M. Allen et al., "Day-and-Night Hybrid Closed-Loop Insulin Delivery in Adolescents With Type 1 Diabetes: A Free-Living, Randomized Clinical Trial," *Diabetes Care, vol.* 39, no. 7, pp. 1168-1174, 2016.

[3] B. Grosman, J. Ilany et al., "Hybrid Closed-Loop Insulin Delivery in Type 1 Diabetes During Supervised Outpatient Conditions," *Journal of Diabetes Science and Technology*, vol. no. 3, pp. 708-713, 2016.

[4] H. Blauw, A. van Bon, R. Koops, J. DeVries, and on behalf of the PCDIAB Consortium; "Performance and safety of an integrated bihormonal artificial pancreas for fully automated glucose control at home," *Diabetes, Obesity and Metabolism*, vol. 18, no. 7, pp. 671-677, 2016.

[5] M. Reddy, P. Herrero et al., "Metabolic Control With the Bio-inspired Artificial Pancreas in Adults With Type 1 Diabetes: A 24-Hour Randomized Controlled Crossover Study," *Journal of Diabetes Science and Technology*, vol. 17, no. 10, pp. 405-413, 2015.

[6] T. T. Ly, A. Roy et al., "Day and Night Closed-Loop Control Using the Integrated Medtronic Hybrid Closed-Loop System in Type 1 Diabetes at Diabetes Camp," *Diabetes Care*, vol. 38, no. 7, pp. 1205-1211, 2015.

[7] T. T. Ly, S. A. Weinzimer, D. M. Maahs, J. L. Sherr, A. Roy, B. Grosman, M. Cantwell, N. Kurtz, L. Carria, L. Messer, R. von Eyben, and B. A. Buckingham, "Automated hybrid closed-loop control with a proportional-integral-derivative based system in adolescents and adults with type 1 diabetes: individualizing settings for optimal performance," *Pediatric Diabetes*, no. April, pp. 1-8, 2016.

[8] R. Nimri, I. Muller et al., "MD-logic overnight control for 6 weeks of home use in patients with type 1 diabetes: randomized crossover trial," *Diabetes Care*, vol. 37, no. 11, pp. 3025-3032, 2014.

[9] R. A. Harvey, E. Dassau, W. C. Bevier, D. E. Seborg, L. Jovanovie, F. J. Doyle III, and H. C. Zisser, "Clinical evaluation of an automated artificial pancreas using zone-model predictive control and health monitoring system." *Diabetes Technology and Therapeutics*, vol. 16, no. 6, pp. 348-357, 2014.

[10] B. P. Kovatchev, E. Renard et al., "Safety of outpatient closed-loop control: first randomized crossover trials of a wearable artificial pancreas," *Diabetes Care*, vol. 37, no. 7, pp. 1789-1796, 2014.

[11] R. S. Parker, E. P. Gatzke, and F. J. Doyle III, "Advanced Model Predictive Control (MPC) for Type I Diabetic Patient Blood Glucose Control," in *Proc 2000 Amer. Cont. Conf. (ACC)*, June 2000, pp. 3483-3487.

[12] E. Dassau, C. C. Palerm, H. Zisser, B. A. Buckingham, L. Jovanovie, and F. J. Doyle III, "In Silico Evaluation Platform for Artificial Pancreatic ß-cell Development—A Dynamic Simulator for Closed-Loop Control with Hardware-in-the-Loop," *Diabetes Technology and Therapeutics*, vol. 11, no. 3, pp. 187-194, 2009.

[13] J. E. Pinsker, J. B. Lee et al., "Randomized crossover comparison of personalized MPC and PID control algorithms for the artificial pancreas," *Diabetes Care, vol.* 39, no. 7, pp. 1135-1142, 2016.

[14] A. Bemporad, M. Morari, V. Dua, and E. N. Pistikopoulos, "The explicit linear quadratic regulator for constrained systems," *Automatica*, vol. 38, pp. 3-20, 2002.

[15] A. Szücs, M. Kvasnica, and M. Fikar, "A memory-efficient representation of explicit MPC solutions," in *Proc 50th IEEE Conf on December and Contr. and Europ. Cont. Conf (CDC-ECC)*, 2011, pp. 1916-1921.

[16] A. Chakrabarty, V. Dinh, M. J. Corless, A. E. Rundell, S. H. Zak, and G. T. Buzzard, "Support vector machine informed explicit nonlinear model predictive control using low-discrepancy sequences," *IEEE Transactions on Automatic Control*, vol. 62, no. 1, pp. 135-148, 2017.

[17] S. Richter, C. N. Jones, and M. Morari, "Computational complexity certification for real-time MPC with input constraints based on the fast gradient method," *IEEE Transactions on Automatic Control*, vol. 57, no. 6, pp. 1391-1403, 2012.

[18] W. P. M. H. Heemels, K. H. Johansson, and P. Tabuada, "An introduction to event-triggered and self-triggered control," in *Proc 51st IEEE Conf on December and Cont. (CDC)*, 2012, pp. 3270-3285.

[19] D. Lehmann, E. Henriksson, and K. H. Johansson, "Event-triggered model predictive control of discrete-time linear systems subject to disturbances," in *Proc Europ. Cont. Conf (ECC)*, 2013, pp. 1156-1161.

[20] D. Bernardini and A. Bemporad, "Energy-aware robust model predictive control based on noisy wireless sensors," *Automatica*, vol. 48, no. 1, pp. 36-44, 2012.

[21] A. Eqtami, D. V. Dimarogonas, and K. J. Kyriakopoulos, "Novel event-triggered strategies for model predictive controllers," in *Proc 50th IEEE Decemberand Contr. and Europ. Cont. Conf (CDC-ECC)*, 2011, pp. 3392-3397. "Event-triggered control for discrete-time systems," in Proc 2010 Amer. Cont. Conf (ACC), 2010, pp. 4719-4724.

[23] M. Jost, M. S. Darup, and M. Mönnigmann, "Optimal and suboptimal event-triggering in linear model predictive control," in Proc Europ. Cont. Conf (ECC), 2015, pp. 1153-1158.

[24] R. Gondhalekar, E. Dassau, H. C. Zisser, and F. J. Doyle III, "Periodic-Zone Model Predictive Control for Diurnal Closed-Loop Operation of an Artificial Pancreas," *Journal of Diabetes Science and Technology*, vol. 7, no. 6, pp. 1446-1460, 2013.

[25] K. van Heusden, E. Dassau, H. C. Zisser, D. E. Seborg, and F. J. Doyle 111, "Control-relevant models for glucose control using a priori patient characteristics," *IEEE Transactions on Biomedical Engineering*, vol. 59, no. 7, pp. 1839-1849, 2012.

[26] R. Hovorka, V. Canonico et al., "Nonlinear model predictive control of glucose concentration in subjects with Type 1 Diabetes," *Physiological Measurement*, vol. 25, no. 4, pp. 905-920, 2004.

[27] C. Dalla Man, R. A. Rizza, and C. Cobelli, "Meal simulation model of the glucose-insulin system," *IEEE Transactions on Biomedical Engineering*, vol. 54, no. 10, pp. 1740-1749, 2007.

[28] M. Eren-Oruklu, A. Cinar, L. Quinn, and D. Smith, "Estimation of future glucose concentrations with subject-specific recursive linear models," *Diabetes Technology and Therapeutics*, vol. 11, no. 4, pp. 243-253, 2009.

[29] R. Gondhalekar, E. Dassau, and F. J. Doyle III, "Periodic zone-MPC with asymmetric costs for outpatient-ready safety of an artificial pancreas to treat type 1 diabetes," *Automatica*, vol. 71, pp. 237-246, 2016.

[30] "Moving-horizon-like state estimation via continuous glucose monitor feedback in MPC of an artificial pancreas for Type I Diabetes," in *Proc 53rd IEEE Conf on December and Cont.*, (CDC), 2014, pp. 310-315.

[31] T. D. Knab, G. Clermont, and R. S. Parker, "Zone model predictive control and moving horizon estimation for the regulation of blood glucose in critical care patients," *9th IFAC Symposium on Adv. Control of Chem. Processes ADCHEM 2015*, vol. 48, no. 8, pp. 1002-1007, 2015.

[32] R. Gillis, C. C. Palerm, H. Zisser, L. Jovanovič, D. E. Seborg, and F. J. Doyle III, "Glucose estimation and prediction through meal responses using ambulatory subject data for advisory mode model predictive control," Journal of Diabetes Science and Technology, vol. 1, no. 6, pp. 825-833, 2007.

[33] D. M. Maahs, P. Calhoun et al., "A randomized trial of a home system to reduce nocturnal hypoglycemia in Type 1 Diabetes," *Diabetes Care*, vol. 37, no. 7, pp. 1885-1891, 2014.

[34] C. Ellingsen, E. Dassau, H. Zisser, B. Grosman, M. W. Percival, L. Jovanovič, and F. J. Doyle III, "Safety Constraints in an Artificial Pancreatic 9-cell: an implementation of model predictive control with insulin on board," *Journal of Diabetes Science and Technology*, vol. 3, no. 3, pp. 536-544, 2009.

[35] L. Magni, D. M. Raimondo, C. Dalla Man, G. De Nicolao, B. Kovatchev, and C. Cobelli, "Model predictive control of glucose concentration in Type 1 Diabetic patients: An in silico trial," *Biomedical Signal Processing and Control*, vol. 4, no. 4, pp. 338-346, 2009.

[36] Y. Wang, E. Dassau, H. Zisser, L. Jovanovič, and F. J. Doyle III, "Automatic bolus and adaptive basal algorithm for the artificial pancreatic ß-cell." *Diabetes Technology and Therapeutics*, vol. 12, no. 11, pp. 879-887, 2010.

[37] B. Grosman, E. Dassau, H. C. Zisser, L. Jovanovič, and F. J. Doyle III, "Zone model predictive control: a strategy to minimize hyper- and hypoglycemic events." *Journal of Diabetes Science and Technology*, vol. 4, no. 4, pp. 961-975, 2010.

[38] M. Breton, A. Farret et al., "Fully integrated artificial pancreas in Type 1 Diabetes: Modular closed-loop glucose control maintains near normoglycemia," *Diabetes*, vol. 61, no. 9, pp. 2230-2237, 2012.

[39] J. B. Lee, E. Dassau, R. Gondhalekar, D. E. Seborg, J. E. Pinsker, and F. J. Doyle III, "An Enhanced MPC (eMPC) Strategy for Auto-mated Glucose Control," *Industrial & Engineering Chemistry Research*, vol. 55, no. 46, pp. 11 857-11 868, 2016.

[40] C. Toffanin, M. Messori, F. Di Palma, G. De Nicolao, C. Cobelli, and L. Magni, "Artificial pancreas: model predictive control design from clinical experience," *Journal of Diabetes Science and Technology*, vol. 7, no. 6, pp. 1470-1483, 2013.

[41] S. D. Patek, L. Magni et al., "Modular Closed-Loop Control of Diabetes," *IEEE Transactions on Biomedical Engineering*, vol. 59, no. 11, pp. 2986-2999, 2012.

[42] E. Dassau, F. Cameron, H. Lee et al., "Real-time hypoglycemia prediction suite using continuous glucose monitoring a safety net for the artificial pancreas," *Diabetes Care*, vol. 33, no. 6, pp. 1249-1254, 2010.

[43] E. Dassau, S. A. Brown et al., "Adjustment of open-loop settings to improve closed-loop results in Type I Diabetes: A multicenter randomized trial," *Journal of Clinical Endocrinology and Metabolism*, vol. 100, no. 10, pp. 3878-3886, 2015.

[44] B. P. Kovatchev, M. Breton, C. Dalla Man, and C. Cobelli, "In Silico Preclinical Trials: A Proof of Concept in Closed-Loop Control of Type 1 Diabetes," *Journal of Diabetes Science and Technology*, vol. 3, no. 1, pp. 44-55, 2009.

[45] M. Andersen, J. Dahl, Z. Liu, and L. Vandenberghe, "Interior-point methods for large-scale cone programming," *Optimization for Machine Learning*, pp. 55-83, 2011.

[46] D. M. Maahs, B. A. Buckingham et al., "Outcome Measures for Artificial Pancreas Clinical Trials: A Consensus Report." *Diabetes Care*, vol. 39, pp. 1175-1179, 2016.

Computer & Hardware Implementation of Disclosure

It should initially be understood that the disclosure herein may be implemented with any type of hardware and/or software, and may be a pre-programmed general-purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks), Zigbee, Bluetooth Low Energy.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, script, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory, flash memory or a random access memory, or any combination of these. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSIONS

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. An artificial pancreas, comprising:
   a glucose sensor configured to output glucose data related to a concentration of glucose in the bloodstream of a subject;
   an insulin pump;
   a memory containing machine readable medium comprising machine executable code having stored thereon instructions for performing a method of delivering insulin; and
   a control system coupled to the memory comprising one or more processors, the control system configured to execute the machine executable code to cause the processor to:
      store, in the memory, a control action for determining an amount of insulin to inject;
      receive, from the glucose sensor, a set of glucose data;
      process the set of glucose data to determine whether an update event is triggered;
      update the control action to determine a first insulin dose value if the update event has been triggered;
      determine a second insulin dose value if the update event has not been triggered, wherein the determination of the second value uses less power than the updating of the control action; and
      send a command to the insulin pump to deliver an amount of insulin based on either the first insulin dose value determined by the updated control action or the second insulin dose value.

2. The artificial pancreas of claim 1, wherein process the glucose data further comprises:
   determine whether a suspension event is warranted; and
   suspend the insulin pump if the suspension event is warranted.

3. The artificial pancreas of claim 2, wherein if suspension is warranted, the control system does not trigger the update event.

4. The artificial pancreas of claim 1, wherein the control action is associated with a Model Predictive Control (MPC) algorithm, and wherein the update of the control action updates the MPC algorithm with state feedback.

5. The artificial pancreas of claim 1, wherein the update event is an insulin-on-board (IOB) upper bound, and wherein if the IOB upper bound is reached, the pump is suspended and the update event is not triggered.

6. The artificial pancreas of claim 1, wherein the update event is triggered when an output estimation error norm $|\Delta y_k|$ exceeds a pre-specified threshold, wherein $y_k$ is a scalar instantaneous measure at time k of blood glucose level y.

7. The artificial pancreas of claim 1, wherein the update event is triggered after a first lmax control actions in $U_{1:N_u|k}^{opt}$ are implemented; wherein l denotes a counter initialized at one; wherein lmax is greater than or equal to 1, and less than or equal to $N_u$, or less than or equal to 3; wherein $U_{1:N_u|k}^{opt}$ denotes an optimal sequence of control actions from time step k+1 to k+$N_u$; and wherein $N_u$ is a control horizon of the control system.

8. The artificial pancreas of claim 1, wherein the artificial pancreas is wearable/implantable in the human body.

9. The artificial pancreas of claim 1, wherein the control system is configured to be idle at least 55% of its operation time.

10. The artificial pancreas of claim 1, wherein the second insulin dose value is determined via a stored previous control action.

11. A method of implementing an artificial pancreas using a control system with one or more processors, the method comprising:
   storing, in a memory, a sequence of control actions for an insulin delivery pump;
   receiving from a glucose sensor, at the control system, a set of glucose data;
   processing, by the control system, the set of glucose data to determine whether an event is triggered for updating the sequence of control actions for the insulin pump to output an updated sequence of control actions by determining a first insulin dose value from the updated sequence of control actions;
   wherein the event is not triggered,
   determining a second insulin dose value via the control system, wherein the determination of the second value uses less power than the updated sequence of control actions; and
   sending either the first insulin dose value or the second insulin dose value to the insulin pump.

12. The method of claim 11, wherein the second insulin dose value is determined via a previous stored sequence of control actions.

13. The method of claim 12, wherein updating the control actions comprises processing the glucose data for state feedback of updating a model predictive control (MPC) algorithm.

14. The method of claim 12, wherein processing, by the control system, the set of glucose data to determine whether an event is triggered further comprises using a linear model to predict the blood glucose based at least on the set of glucose data.

15. The method of claim 12, wherein the memory is flash memory.

16. The method of claim 12, wherein the control system is on an embedded platform or mobile device.

17. The method of claim 12, wherein the control system is on an insulin pump.

18. The method of claim 12, wherein the control system is configured to be idle at least 55% of its operation time.

19. The artificial pancreas of claim 1, further comprising storing the updated control action in the memory.

* * * * *